US009346846B1

(12) United States Patent
Herzon et al.

(10) Patent No.: US 9,346,846 B1
(45) Date of Patent: May 24, 2016

(54) ANTI-CANCER COMPOUNDS AND METHODS FOR TREATING CANCER

(71) Applicant: YALE UNIVERSITY, New Haven, CT (US)

(72) Inventors: Seth Herzon, New Haven, CT (US); Christina Woo, Berkeley, CA (US); Peter M. Glazer, Guilford, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 14/557,834

(22) Filed: Dec. 2, 2014

Related U.S. Application Data

(60) Provisional application No. 61/910,593, filed on Dec. 2, 2013.

(51) Int. Cl.
| | | |
|---|---|---|
| A61K 31/351 | (2006.01) |
| C07D 309/02 | (2006.01) |
| C07H 15/26 | (2006.01) |
| A61K 45/06 | (2006.01) |
| C07H 5/06 | (2006.01) |
| A61K 47/48 | (2006.01) |
| A61K 31/7008 | (2006.01) |

(52) U.S. Cl.
CPC ............ *C07H 15/26* (2013.01); *A61K 31/7008* (2013.01); *A61K 45/06* (2013.01); *A61K 47/48061* (2013.01); *C07H 5/06* (2013.01)

(58) Field of Classification Search
CPC ............................ A61K 31/351; C07D 309/02
USPC ............................ 549/200, 356; 514/451, 460
See application file for complete search history.

(56) References Cited

PUBLICATIONS

Woo et al (2010): STN International HCAPLUS database, Columbus (OH), Accession No. 2010: 170328.*
Nicolaou et al (2009): STN International HCAPLUS database, Columbus (OH), Accession No. 2009: 915656.*
Tuszynski GP, et al. Thrombospondin Promotes Platelet Aggregation. Blood, 1988;72(1):109-115.
Morrison SL, et al. Chimeric human antibody molecules: Mouse antigen-binding domains with human constant region domains. Proc Natl Acad Sci, USA; 1984;81:6851-6855.
Boulianne GL, et al. Production of functional chimaeric mouse/human antibody. Nature, 1984;312:643-646.
Tan LK, et al. A Human-Mouse Chimeric Immunoglobulin Gene With a Human Variable Region is Expressed in Mouse Myeloma Cells. The Journal of Immunology, 1985;135(5):3564-3567.
Whittle N, et al. Expression in COS cells of a mouse-human chimaeric B72.3 antibody. Protein Engineering, 1987;1 (6):499-505.
Liu AY, et al. Chimeric mouse-human IgG1 antibody that can mediate lysis of cancer cells. Proc Natl Acad Sci, USA, 1987;84:3439-3442.

Jones PT, et al. Replacing the complementarity-determining regions in a human antibody with those from a mouse. Nature, 1986;321:522-525.
Verhoeyen M, et al. Reshaping HUman Antibodies: Grafting an Antilysozyme Activity. Science, 1987;239:1534-1536.
Hale G, et al. Remission Induction in Non-Hodgkin Lymphoma With Reshaped Human Monoclonal Antibody Campath-1H. The Lancet, 1988;2:1394-1399.
Queen C, et al. A humanized antibody that binds to the interleukin 2 receptor. Proc Natl Acad Sci USA, 1989;86:10029-10033.
Nicolaou KC, et al. Oxidation of Silyl Enol Ethers by Using IBX and IBX*N-Oxide Complexes: A Mild and Selective Reaction for the Synthesis of Enones. Angew Chem Int Ed, 2002;41(6):996-1000.
Ito Y, et al. Synthesis of alpha,beta-Unsaturated Carbonyl Compounds by Palladium(II)-Catalyzed Dehydrosilylation of Silyl Enol Ethers. J Org Chem, 1978;43(5):1011-1013.
Ryu I, et al. A Ketone-Enone Conversion Via the Reaction of Enol Silyl Ethers With DDQ. Tetrahedron Letters, 1978;37:3455-3458.
Frohn M, et al. A Mild and Efficient Epoxidation of Olefins Using in Situ Generated Dimethyldioxirane at High pH. J Org Chem, 1998;63:6425-6426.
Gholap SL, et al. Synthesis of the Fully Glycosylated Cyclohexenone Core of Lomaiviticin A. Organic Letters, 2009;11(19):4322-4325.
Posner GH, Haines SR. Regents. Stereospecific Alkylation at C-6 of A Pyranose Sugar. Tetrahedron Letters, 1985;26(15):1823-1826.
Woo CM, et al. Development of a Convergent Entry to the Diazofluorene Antitumor Antibiots: Enantioselective Synthesis of Kinamycin F. J Am Chem Soc, 2010;132:2540-2541.

(Continued)

*Primary Examiner* — Golam M M Shameem
(74) *Attorney, Agent, or Firm* — Henry D. Coleman; R. Neil Sudol

(57) ABSTRACT

The present invention is directed to novel anti-cancer compounds and methods of treating and/or inhibiting cancer in patients, including metastatic cancer, recurrent cancer and drug resistant cancers, including multiple drug resistant cancers. Compounds according to the present invention provide anti-cancer activity, at least in part, by virtue of their nucleotide intercalating activity through the use of analogs of (−)lomaiviticin A, a potent anticancer agent which exhibits cytotoxicity through its principal mechanism of cleavage and to a lesser extent, its intercalation of cellular polynucleotides, especially DNA. In additional embodiments, compounds according to the present invention are also conjugated and/or linked to other bioactive agents, especially agents which selectively target cancer cells (cancer cell targeting moiety or CCTM) to target and increase the delivery of the anticancer agent to the cancer cell. These targeting agents include folate receptor-targeted moieties, other cancer binding moieties such as PMSA binding moieties as otherwise described herein and antibodies, including single chain variable fragment antibodies (scFv antibodies). Pharmaceutical compositions based upon these novel compounds are also disclosed pursuant to the present invention. Methods of treating, inhibiting and/or reducing the likelihood of cancer, including metastatic and recurrent cancer and drug resistant, including multiple drug resistant cancer in a patient are also disclosed.

8 Claims, 30 Drawing Sheets

(56) References Cited

PUBLICATIONS

Herzon SB, et al. 11-Step Enantioselective Synthesis of (−)-Lomaiviticin Aglycon. J Am Chem Soc, 2011;133:7260-7263.

Woo CM, et al. Development of Enantioselective Synthetic Routes to (−)-Kinamycin F and (−)-Lomaiviticin Aglycon. J Am Chem Soc, 2012;134(41):17262-17273.

Ryu I, et al. A Ketone-Enone Conversion Via the Reaction of Enol Silyl Ethers With DDQ. Tetrahedron Letters, 1978;19(37):3455-3458.

Reich HJ, et al. Organoselenium Chemistry. Conversion of Ketones to Enones by Selenoxide Syn Elimination. Journal of the American Chemical Society, 1975;97:5434-5447.

Colis, L. C. et al.; The cytotoxicity of (−)-lomaiviticin A arises from induction of double-strand breaks in DNA. Nature Chemistry Jun. 2014; 6:504-510.

* cited by examiner

Synthesis of Basic Cyclohexene Building Block for ILM Group

Preparation of Carbohydrate for ILM Group

Deoxy Analog of ILM Group

Synthesis of Chimeric Molecule with Folate CCTM Group

Lomaiviticin A Linked to Folate Targeting Moiety

FIGURE 15
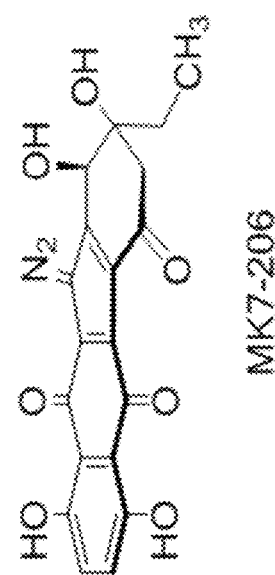
MK7-206
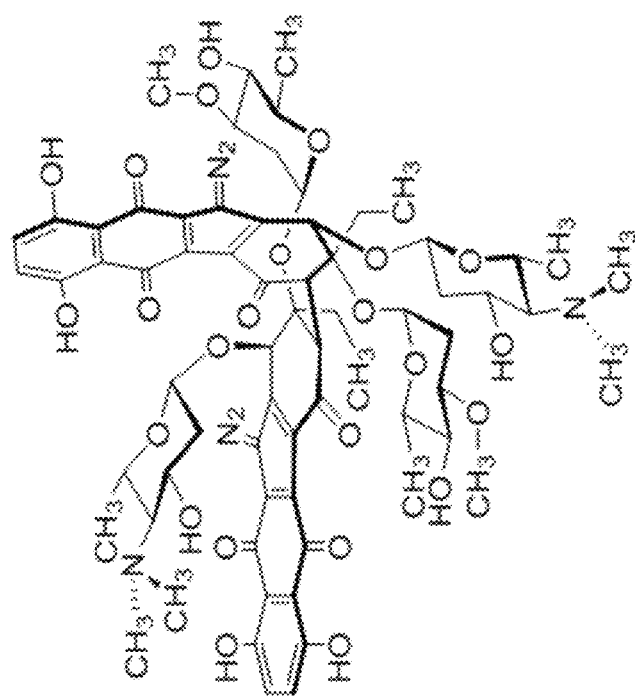
(−)-lomaiviticin A

BRCA2-deficient (VC8 and Eufa.423) cells are more sensitive to LA

KU80-deficient (XRS6) cells are more sensitive to LA

DNApk-deficient (SKID) cells are more sensitive to LA

BRCA1-deficient (HCC1937 and UWB1.289) cells are not sensitive to LA

FancD2-deficient (PD20) cells are not sensitive to LA

XPA-deficient (XP20S) cells are not sensitive to LA

MLH1-deficient (HCT116) cells are not sensitive to LA

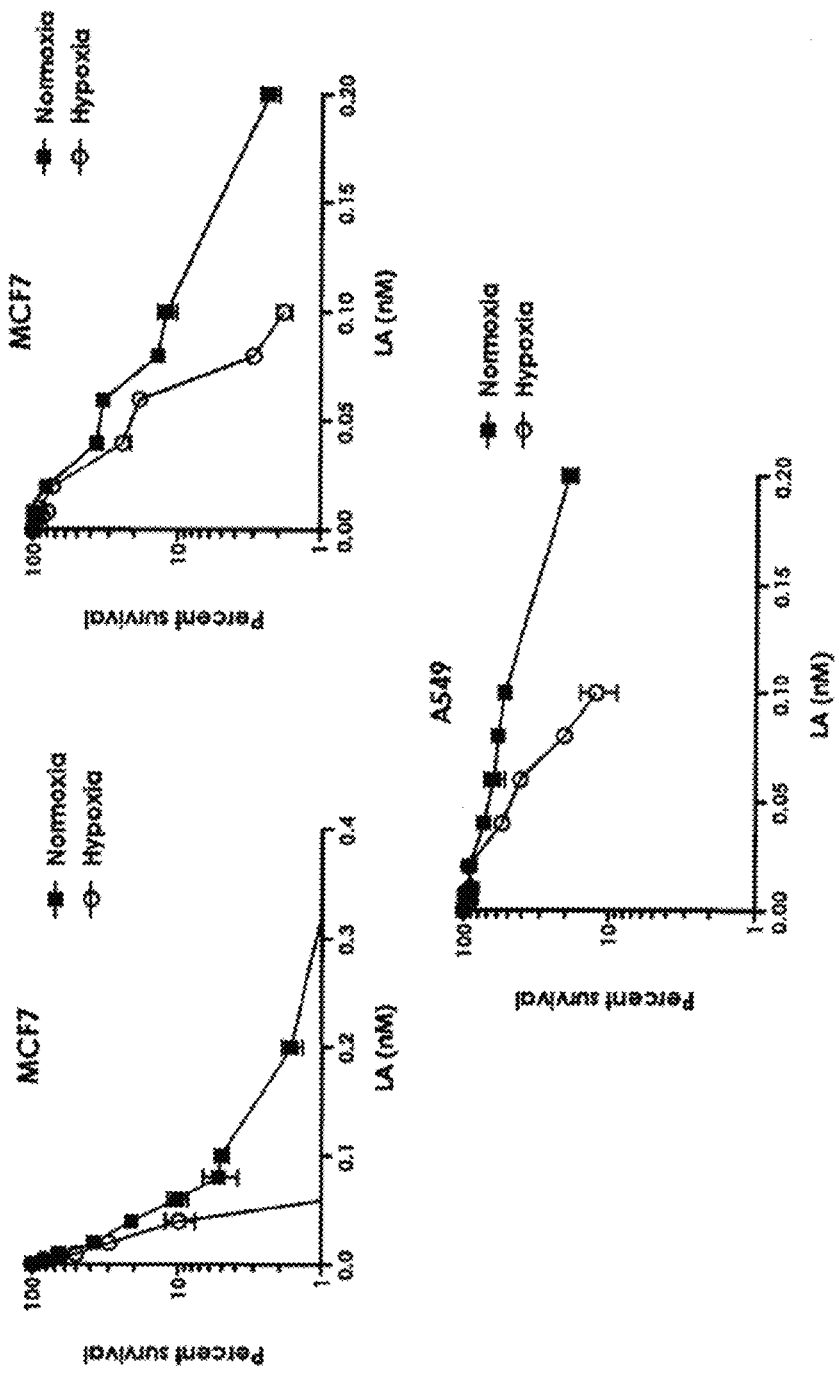

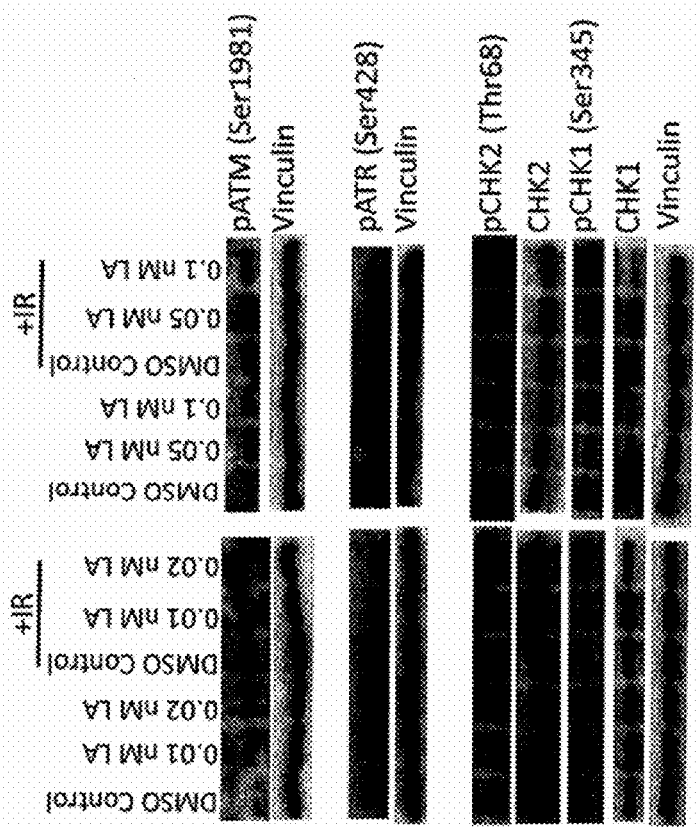

FIGURE 27

| Cell line | Origin | Deficiency | LC50 (pM) Proficient | LC50 (pM) Deficient | LC90 (pM) Proficient | LC90 (pM) Deficient |
|---|---|---|---|---|---|---|
| Peo1 | Human ovarian adenocarcinoma | BRCA2 | 7 | 3 | 16 | 7 |
| DLD1 | Human colorectal adenocarcinoma | BRCA2 | 3 | 3 | 30 | 11 |
| V-C8 | CHO | BRCA2 | 5 | <2 | 10 | 2 |
| EUFA423 | Human fibroblasts | BRCA2 | 15 | 9 | 35 | 21 |
| U251 | Human glioblastoma | PTEN | 15 | <2 | 30 | <2 |
| XRS6 | CHO | KU80 | 25 | 3 | 35 | 7 |
| 50D | SCID mouse fibroblasts | DNAPK | 25 | 15 | 35 | 25 |
| 5849 | Human fibroblasts | ATM | 3 | 1 | >10 | 6 |
| HCT116 | Human colorectal carcinoma | MLH1 | 4 | 4 | 5 | 7 |
| HCC1937 | Human breast ductal carcinoma | BRCA1 | 70 | 80 | 100 | >100 |
| UWB1289 | Human ovarian carcinoma | BRCA1 | 4 | 5 | 20 | 20 |
| PD20 | Human lymphoblastoid | FANCD2 | 7 | 7 | 15 | 15 |
| XP20S | Human fibroblasts | XPA | 6 | 6 | 15 | 15 |

Table 1

| Cell line | Origin | Deficiency | LC50 (pM) Proficient | LC50 (pM) Deficient | LC90 (pM) Proficient | LC90 (pM) Deficient |
|---|---|---|---|---|---|---|
| Peo1 | Human ovarian adenocarcinoma | BRCA2 | 50 | 15 | 90 | 30 |
| DLD1 | Human colorectal adenocarcinoma | BRCA2 | >100 | 15 | >100 | 40 |
| VC8 | CHO | BRCA2 | 50 | 5 | 90 | 15 |
| EUFA423 | Human fibroblasts | BRCA2 | | | | |
| U251 | Human glioblastoma | PTEN | 45 | 15 | >50 | 25 |
| XRS6 | CHO | KU80 | 45 | 35 | >60 | 55 |
| SCID | SCID mouse fibroblasts | DNAPK | | | | |
| S849 | Human fibroblasts | ATM | 25 | 15 | 50 | 50 |
| HCT116 | Human colorectal carcinoma | MLH1 | 30 | 50 | 70 | 90 |
| HCC1937 | Human breast ductal carcinoma | BRCA1 | 50 | 80 | >100 | >100 |
| UWB1289 | Human ovarian carcinoma | BRCA1 | | | | |
| PD20 | Human lymphoblastoid | FANCD2 | | | | |
| XP20S | Human fibroblasts | XPA | | | | |

Table 2

FIGURE 29

| Cell line | Origin | Deficiency | % Survival at 4 pM LA Proficient | % Survival at 4 pM LA Deficient | % Survival at 10 pM LA Proficient | % Survival at 10 pM LA Deficient |
|---|---|---|---|---|---|---|
| Peo1 | Human ovarian adenocarcinoma | BRCA2 | 65 | 29 | 32 | 2 |
| DLD1 | Human colorectal adenocarcinoma | BRCA2 | 41 | 21 | 31 | 14 |
| VC8 | CHO | BRCA2 | 58 | 5 | 11 | 1 |
| EUFA423 | Human fibroblasts | BRCA2 | 100 | 77 | 84 | 45 |
| U251 | Human glioblastoma | PTEN | 77 | 0 | 72 | 0 |
| XRS6 | CHO | KU80 | 87 | 46 | 75 | 0.5 |
| SCID | SCID mouse fibroblasts | DNAPK | 100 | 84 | 83 | 45 |
| S849 | Human fibroblasts | ATM | 32 | 9 | 15 | 5 |
| HCT116 | Human colorectal carcinoma | MLH1 | 20 | 29 | 1 | 4 |
| HCC1937 | Human breast ductal carcinoma | BRCA1 | 64 | 77 | 11 | 15 |
| UWB1.289 | Human ovarian carcinoma | BRCA1 | 48 | 66 | 13 | 23 |
| PD20 | Human lymphoblastoid | FANCD2 | 59 | 59 | 53 | 39 |
| XP20S | Human fibrobasts | XPA | 65 | 65 | 24 | 16 |

Table 3

FIGURE 30
MK7-206

| Cell line | Origin | Deficiency | % Survival at 20 nM MK7 Proficient | Deficient | % Survival at 60 nM MK7 Proficient | Deficient |
|---|---|---|---|---|---|---|
| Pea1 | Human ovarian adenocarcinoma | BRCA2 | 79 | 22 | 40 | 1 |
| DLD1 | Human colorectal adenocarcinoma | BRCA2 | 89 | 25 | 83 | 0.3 |
| VC8 | CHO | BRCA2 | 84 | 1 | 39 | 0 |
| EUFA423 | Human fibroblasts | BRCA2 | | | | |
| U251 | Human glioblastoma | PTEN | 82 | 16 | ~40 | 0 |
| XRS6 | CHO | KU80 | 99 | 64 | 45 | 7 |
| 50D | SCID mouse fibroblasts | DNAPK | | | | |
| 5849 | Human fibroblasts | ATM | 58 | 46 | 24 | 9 |
| HCT116 | Human colorectal carcinoma | MLH1 | 86 | 86 | 18 | 32 |
| HCC1937 | Human breast ductal carcinoma | BRCA1 | 67 | 85 | 47 | 62 |
| UWB1.289 | Human ovarian carcinoma | BRCA1 | | | | |
| PD20 | Human lymphoblastoid | FANCD2 | | | | |
| XP20S | Human fibroblasts | XPA | | | | |

Table 4

ANTI-CANCER COMPOUNDS AND METHODS FOR TREATING CANCER

This non-provisional application claims priority from application No. 61/910,593, filed Dec. 2, 2013 of identical title, the entire contents of which are incorporated by reference in their entirety herein.

RELATED APPLICATIONS AND GRANT SUPPORT

This invention was made with government support under GM090000 awarded by National Institutes of Health. The government has certain rights in the invention.

FIELD OF THE INVENTION

The present invention is directed to novel anti-cancer compounds and methods of treating, reducing the likelihood and/or inhibiting cancer in patients, including metastatic cancer, recurrent cancer and drug resistant cancers, including multiple drug resistant cancers. Compounds according to the present invention provide anti-cancer activity, at least in part, by virtue of their nucleotide cleavage and intercalating activity through the use of analogs of (–) lomaiviticin A, a potent anticancer agent which exhibits cytotoxicity through its mechanism of cleaving (breakage) and intercalating cellular polynucleotides, especially DNA. In additional embodiments, compounds according to the present invention are also conjugated and/or linked to other bioactive agents, especially agents which selectively target cancer cells (cancer cell targeting moiety or CCTM) to target and increase the delivery of the anticancer agent to the cancer cell. These targeting agents include folate receptor-targeted moieties, other cancer binding moieties such as PMSA binding moieties as otherwise described herein and antibodies, including single chain variable fragment antibodies (scFv antibodies). Pharmaceutical compositions based upon these novel compounds are also disclosed pursuant to the present invention. Methods of treating, inhibiting and/or reducing the likelihood of cancer, including metastatic cancer in a patient are also disclosed.

BACKGROUND OF THE INVENTION

Lomaiviticin A is a complex metabolite with potent cytotoxic anticancer activity. The mechanism of this activity is by virtue of Lomaivitacin A cleaving and intercalating polynucleotides (principally, DNA) and disrupting the cellular processes, especially including cell growth, and selectively producing cancer cell death. Notwithstanding that activity, to date, there has yet to be a therapeutic approach relying on Lomaiviticin A as a cleaving/intercalating agent which delivers/targets these cytotoxic agents to a cancer cell and produces cancer cell death with the level of activity pursuant to the present invention.

BRIEF DESCRIPTION OF THE INVENTION

The present invention relates, in the first instance, to compounds which are analogs of (–) lomaiviticin A, which find use as anticancer agents pursuant to the present invention. Compounds according to the present invention are based upon a chemical structure which comprises at least one intercalating moiety (which functions as having one or preferably both cleavage and/or intercalating activity) which is an analog of lomaiviticin A (ILM) to which is bonded at least one cancer cell targeting moiety (CCTM) either directly or through a linker moiety L which is cleavable or non-cleavable, depending on the CCTM used in the compound to bind the compound to a cancer cell. Compounds according to the present invention comprise from one to eight (ILM) moieties (preferably one (ILM) group) to which is/are covalently attached from 1 to 15 (CCTM) groups, preferably from 1 to 8 (CCTM) groups, more preferably from 1 to 4 (CCTM) groups, each (CCTM) group being optionally covalently attached to a (ILM) group through a linker molecule (L). The linker molecule may be non-cleavable or cleavable, depending upon the function of the (CCTM) group to which is attached the (ILM) group.

In a first embodiment, the present invention is directed to compounds according to the chemical structure:

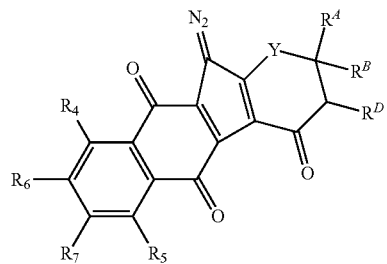

where Y is a bond or CH—$R^S$;

$R_4$ and $R_5$ are each independently OH, $C_1$-$C_3$ alkyl, O—($C_1$-$C_3$)alkyl, a OC(O)—($C_1$-$C_3$) alkyl group, a C(O)O—($C_1$-$C_3$) or L-CCTM (preferably both $R_4$ and $R_5$ are OH);

$R_6$ and $R_7$ are each independently H, $C_1$-$C_3$ alkyl, OH, O—($C_1$-$C_3$)alkyl, halo (F, Cl, Br or I), a OC(O)—($C_1$-$C_3$) alkyl group, a C(O)O—$C_1$-$C_3$) or L-CCTM;

$R^A$ and $R^B$ are each independently H, OH, $C_1$-$C_3$ alkyl (preferably, ethyl or H and ethyl) or L-CCTM;

$R^D$ is H, $C_1$-$C_3$ alkyl, O($C_1$-$C_3$) alkyl, an optionally substituted aryl group or forms a dimer compound with the compound to which $R^D$ is attached (in certain preferred embodiments, $R^D$ is H or the compound to which $R^D$ is attached and $R^D$ form a dimer);

$R^S$ is H, OH, a

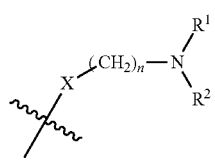

group where n is 0, 1, 2, 3, 4, or 5 and one or more (preferably one) of the methylene groups when present are optionally substituted with OH, $OCH_3$ or $CH_3$, or $R^S$ is a sugar moiety containing a 4-amino group which is optionally substituted with a L-CCTM group or one or two $C_1$-$C_3$ alkyl groups which alkyl groups may be optionally substituted with one or two alcohol groups, preferably $R^S$ is a sugar moiety according to the chemical structure:

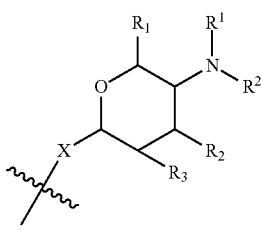

where X is O, S, N—$R^N$ or $CH_2$ (preferably O);
$R^N$ is H or a $C_1$-$C_3$ alkyl group (preferably H);
$R^1$ and $R^2$ are each independently H, a $C_1$-$C_3$ alkyl group optionally substituted with one or two alcohol groups (preferably methyl) or a L-CCTM group (preferably R1 and R2 are each H or H and $CH_3$);
$R_1$, $R_2$ and $R_3$ are each independently H, OH, a halo group (F, Cl, Br, I), O—($C_1$-$C_3$)alkyl, a $C_1$-$C_3$ alkyl, a $C_2$-$C_4$ acyl group, a OC(O)—($C_1$-$C_3$) alkyl group, a C(O)O—$C_1$-$C_3$ alkyl group or a L-CCTM group;
L is a bond or a linker group; and
CCTM is a cancer cell targeting moiety which binds to a cancer cell in a patient, or a pharmaceutically acceptable salt, stereoisomer, solvate or polymorph thereof.

In certain embodiments, $R^S$ is a group according to the chemical structure:

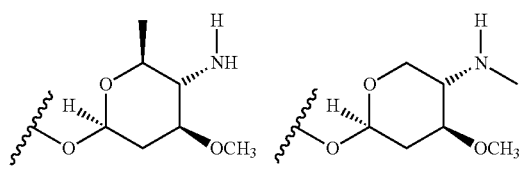

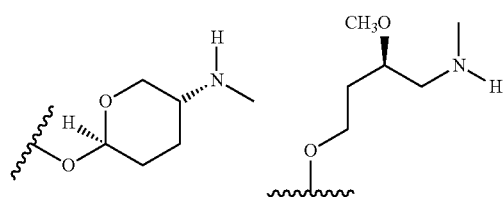

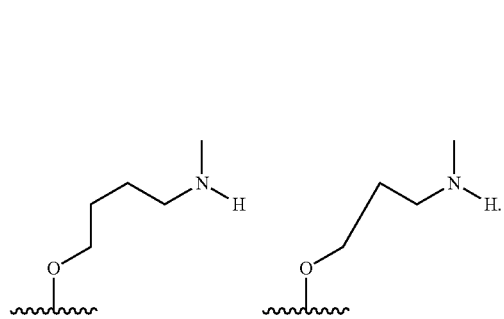

In another embodiment, the present invention is directed to a compound according to the chemical structure:

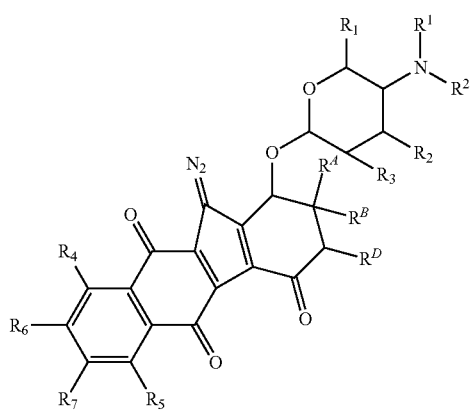

where $R^1$ and $R^2$ are each independently H, a $C_1$-$C_3$ alkyl group (preferably methyl) or a L-CCTM group;
$R_1$, $R_2$ and $R_3$ are each independently H, OH, O—($C_1$-$C_3$) alkyl, a $C_1$-$C_3$ alkyl or a L-CCTM group;
$R_4$ and $R_5$ are each independently OH, $C_1$-$C_3$ alkyl, O—($C_1$-$C_3$)alkyl or L-CCTM (preferably both are OH);
$R_6$ and $R_7$ are each independently H, $C_1$-$C_3$ alkyl, OH, O—($C_1$-$C_3$)alkyl, halo (F, Cl, Br or I) or L-CCTM;
$R^A$ and $R^B$ are each independently H, $C_1$-$C_3$ alkyl (preferably, ethyl or H and ethyl) or L-CCTM;
$R^D$ is H or forms a dimeric compound with the compound to which RD is attached (preferably $R^D$ and the compound to which $R^D$ is attached are identical and attached at the same position);
L is absent (a bond) or a linker group (preferably, a cleavable linker group); and CCTM is a cancer cell targeting moiety which binds to a cancer cell in a patient, or a pharmaceutically acceptable salt, stereoisomer, solvate or polymorph thereof.

In another embodiment, the present invention is directed to compounds according to the chemical structure:

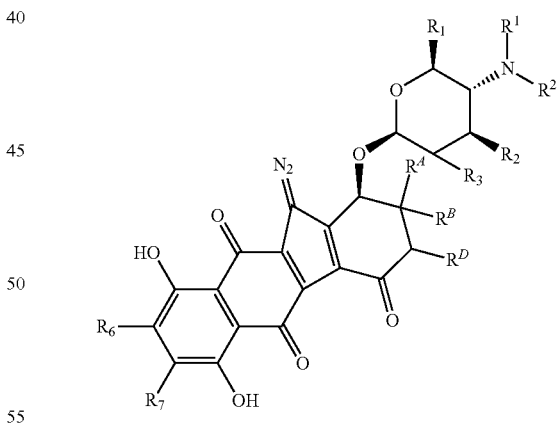

Where $R^1$ and $R^2$ are each independently H, $CH_3$ or L-CCTM (preferably, both are $CH_3$),
$R_1$ is H, $C_1$-$C_3$ alkyl or L-CCTM, (preferably $CH_3$);
$R_2$ is H, OH or L-CCTM, (preferably OH);
$R_3$ is H, $CH_3$, or L-CCTM, (preferably H);
$R_6$ and $R_7$ are each independently H or L-CCTM;
$R^A$ and $R^B$ are each independently H, ethyl, or L-CCTM; and $R^D$ is H or forms a dimeric compound with the compound to which RD is attached (preferably $R^D$ and the compound to which $R^D$ is attached are identical and attached at the same position);

L is absent (a bond) or a linker group, which may be a cleavable linker group or a non-cleavable linker group depending on the CCTM group; and CCTM is a cancer cell targeting moiety which binds to a cancer cell in a patient, or a pharmaceutically acceptable salt, stereoisomer, solvate or polymorph thereof.

In further embodiments according to the present invention, compounds according to the present invention are represented by the following structures:

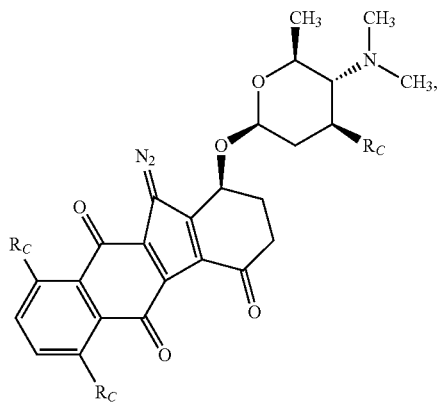

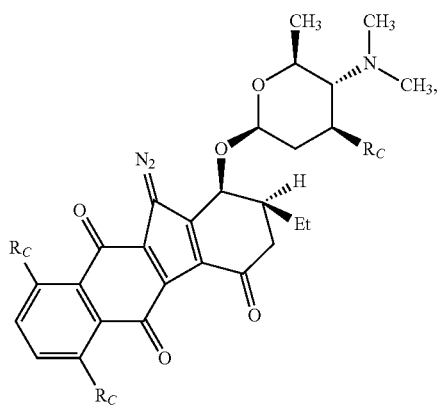

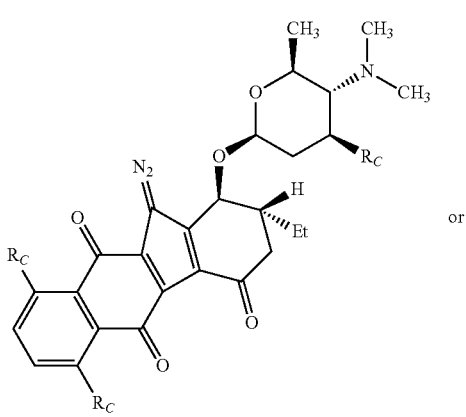

or

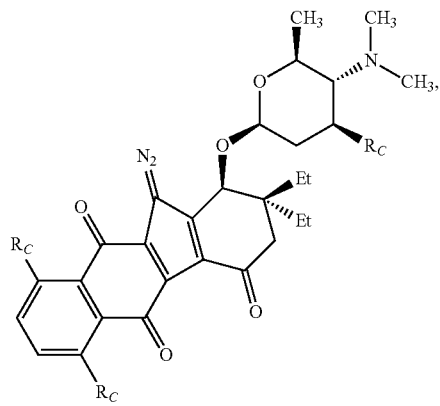

Where each $R_C$ is independently OH or a L-CCTM group as described above. Preferably at least one $R_C$ group is a L-CCTM group.

In an alternative embodiment, preferred dimer compounds pursuant to the present invention include the following:

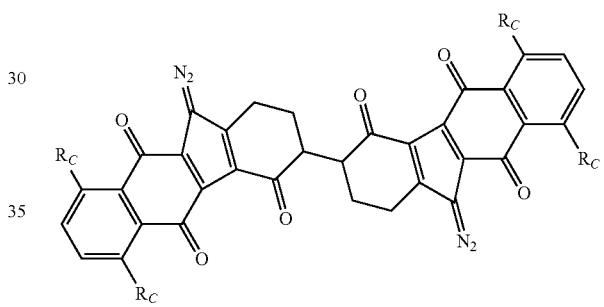

or

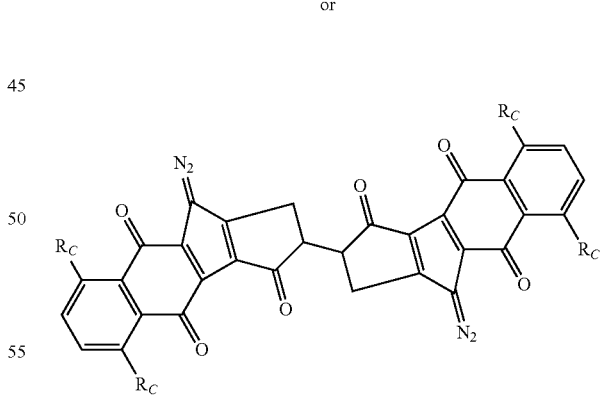

where each $R_C$ is independently OH or a L-CCTM group as described above. Preferably at least one $R_C$ group is a L-CCTM group.

In still other embodiments pursuant to the present invention, preferred dimer compounds incorporate a sugar group according to the following chemical structures:

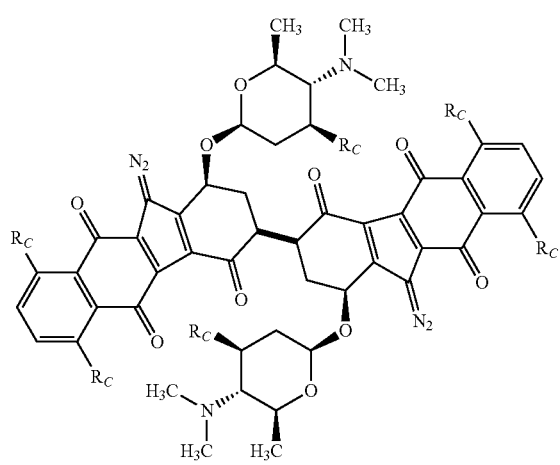
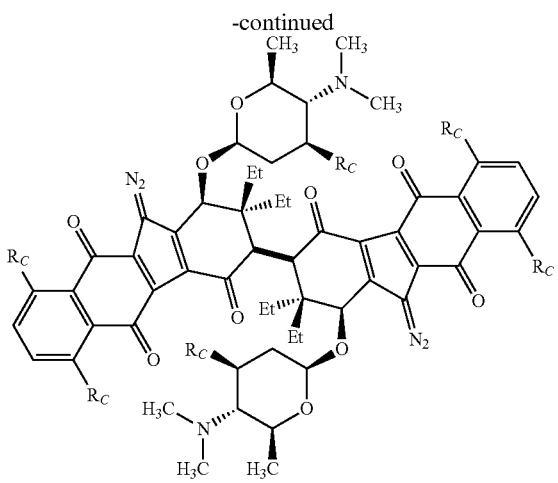
Where each $R_C$ is independently OH or a L-CCTM group as described above. Preferably at least one $R_C$ group is a L-CCTM group.
In yet another embodiment, the present invention relates to compounds according to the chemical structure:
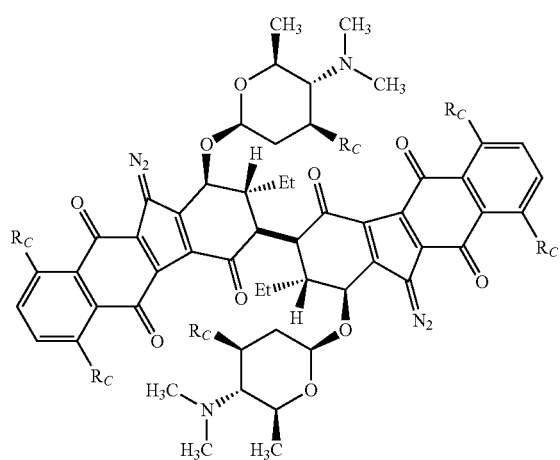
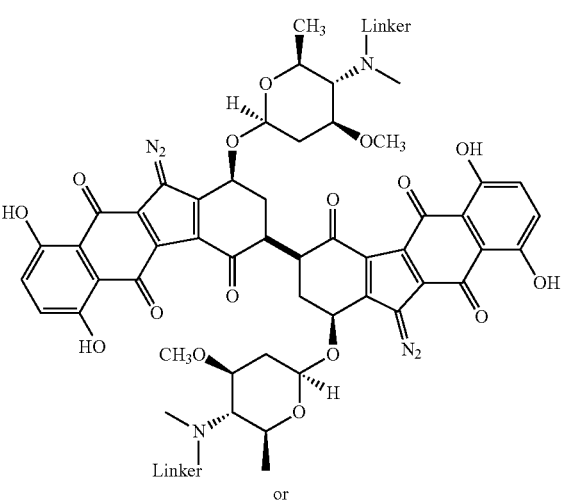
or
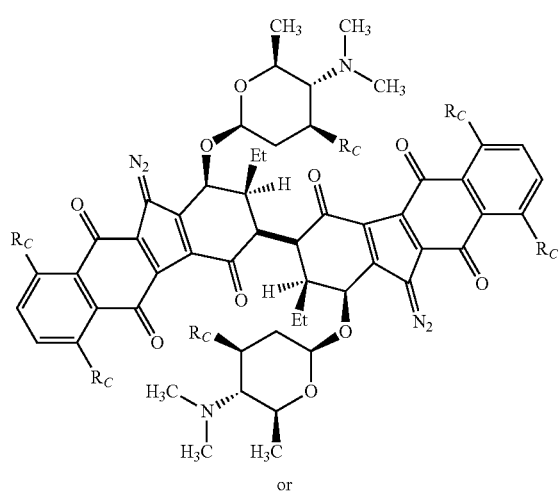
or
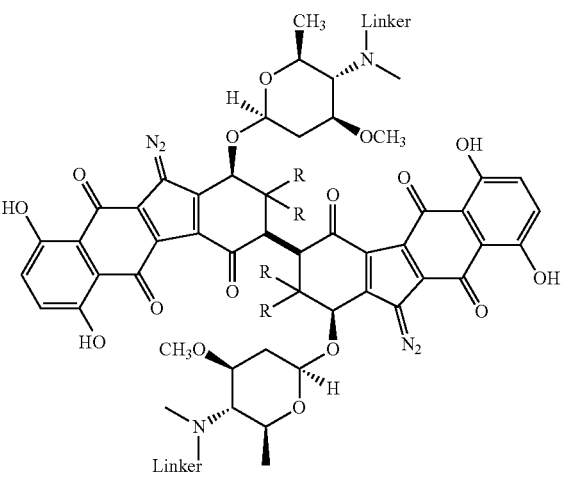
Where R is H or $CH_3$ with the proviso that at least one R is $CH_3$ (preferably, all R are $CH_3$); and Linker is a linker group as otherwise herein optionally substituted with a CCTM group.

In yet another embodiment pursuant to the present invention, compounds may be represented by the chemical structure:

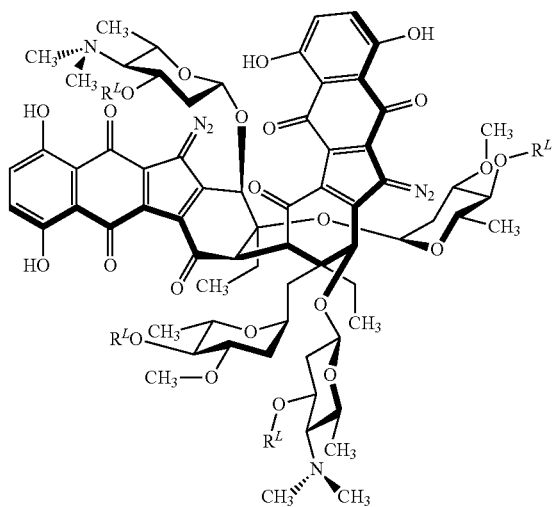

where $R^L$ is H or a L-CCTM group as described herein, or a pharmaceutically acceptable salt, stereoisomer, solvate or polymorph thereof In certain embodiments, the linker group is a non-cleavable linker group as otherwise described herein (in some instances a polyethylene glycol group or between 2 and 12 ethylene glycol units, often 4 to 8 ethylene glycol unts) or a cleavable linker group, more preferably a peptide linker group or a group which contains a cleavable disulfide group as otherwise described herein. In the case of the CCTM group, this group is preferably selected from the group consisting of a folate receptor binding moiety, a monoclonal antibody (especially a humanized monoclonal antibody) such as herceptin or an antibody fragment (FAB), including a single chain variable fragment (scFv) antibody which binds to cancer cells, a PSMA binding moiety or a YSA peptide (YSAYPDS-VPMMS (SEQ ID NO: 1)) as otherwise described in greater detail herein. When the CCTM group is a folate receptor binding moiety, the linker group L is preferably non-cleavable. In instances where the CTM group is an antibody or antibody-related moiety as described above, the linker group L is preferably a cleavable group.

The present invention also relates to pharmaceutical compositions comprising an anticancer effective amount of a compound according to the present invention as described herein, in combination with a pharmaceutically acceptable carrier, additive and/or excipient, optionally in combination with an additional anticancer agent as otherwise described herein.

In a further aspect of the invention, compounds according to the present invention are used to treat and/or reduce the likelihood of cancer in a patient in need thereof and to treat or reduce the likelihood that a cancer will metastasize or that a cancer in remission will reoccur (recurrence). The method of treating cancer comprises administering to a patient in need an effective amount of a compound as otherwise described herein in combination with a pharmaceutically acceptable carrier, additive or excipient, optionally in further combination with at least one additional agent which is effective in treating cancer, metastatic cancer, recurrent cancer or one or more of its secondary conditions or effects.

The present invention also relates to a method for inhibiting cancer to reduce or inhibit the spread or metastasis of the cancer into other tissues of the patients' body, especially including bones, the lymph (lymph nodes) system, bladder, vas deferens, kidneys, liver, lungs and brain, among others. Methods for treating recurrent cancer and/or reducing the likelihood of a cancer recurring after remission are additional method embodiments according to the present invention.

In another embodiment, the present invention also relates to the use of the compounds as otherwise described herein for the treatment of cancers wherein DNA repair factors of the cells are deficient/unexpressed by the cells (DNA damage response deficient or DDR deficient cells) or where the cells are hypoxic. In this aspect of the invention, cells which are deficient in one or both of non-homologous enjoining and homologous recombination DNA repair mechanisms (either because of mutation or down regulation) are found to be more susceptible to compounds according to the present invention, especially including (−) lomaiviticin A and MK7-206. These DNA repair mechanisms involve DNA repair factors including one or more of KU80, pten, BRAC2, DNApk, ATM, PALB2 and RAD51 paralogs, among a number of others. In this aspect of the present invention, a cancer in a patient or subject to be treated is determined (diagnosed) to be deficient in a DNA repair mechanism (by biopsy, genetic testing evidencing a mutation in the gene, or assaying for biomarkers and showing down regulation of same, etc) as identified by known DNA repair factors, including one or more of the above-mentioned DNA repair factors, among others (DDR deficient) and/or the cancer to be treated is determined or identified to be hypoxic and the patient or subject in need is administered at least one compound according to the present invention, optionally in combination with at least one additional anticancer agent. This treatment may optionally occur in the presence of radiation therapy (often where the cancer is not hypoxic). Preferred compounds for use in this aspect of the present invention include (−)-lomaivitacin A and MK-207 (FIG. 15), although numerous other compounds according to the present invention may be used in this aspect of the invention, optionally in combination with at least one additional anticancer agent. Although any cancer as otherwise described herein may be treated in this aspect of the present invention, it is noted that ovarian cancer, breast cancer, colon cancer, head, neck, pancreatic cancer, prostate cancer, melanoma, brain cancer/central nervous system cancers (glioma) often express reduced levels of these DNA repair factors, thus rendering them more susceptible to treatment with any one or more compounds according to the present invention, especially including (−)-lomaivitacin A and MK-207. In addition, any cancer cell as otherwise described herein may be hypoxic or rendered hypoxic and these hypoxic cells are particularly susceptible to therapy using one or more of the compounds according to the present invention.

In still another embodiment, the present invention relates to a method of treating cancer in a patient or subject comprising administering the patient or subject an inhibitor of any one or more of a DNA repair factor such as KU80, pten, BRAC2, DNApk, ATM, PALB2 and/or RAD51 paralogs in combination with at least one compound according to the present invention. In this aspect of the present invention a cancer which expresses one or more DNA repair factors such as KU80, pten, BRAC2, DNApk, ATM, PALB2 and/or RAD51 paralogs can be administered an inhibitor of one or more of these DNA repair factors, often a siRNA (small inhibitory RNA) which results in the DNA repair factor being underexpressed in the cancer cell, thus rendering the cell far more susceptible to inhibition/treatment with a compound according to the present invention, especially including (−)-lomaiviticin A and/or MK-207, among numerous other anticancer compounds as disclosed herein. One or more of these compounds may be administered alone or in combination with a traditional anticancer agent, preferably a compound which has a DNA damaging mechanism other than through DNA cleavage/intercalation to provide effective anticancer treatment.

BRIEF DESCRIPTION OF THE FIGURES

FIG. 15 shows the chemical structure of (−)-lomaiviticin A (LA) and compound MK7-206 which are used in certain preferred aspects of the present invention to inhibit and/or treat cancers which are deficient (exhibit low levels of expression or undetectable levels of expression) of one or more of KU80, pten, BRAC2 and DNApk.

FIG. 25 shows the effect of (−)-lomaiviticin A (LA) on hypoxic MCF7 and A549 cells. The hypoxic cells are more sensitive to LA than are the normal (normoxia) cells.

FIG. 26 shows the effect of LA treatment in MCF7 cells on pATM and pCHK2 (increase) and pATR and pCHK1 (no increase) in a western blot analysis.

FIGS. 27-30 show several tables (Table 1-4) which tabulates the effect of (−)-lomaiviticin A or MK7-206 on the various cell lines tested. FIG. 27 (Table 1) shows the effect of (−)-lomaiviticin A (LA) on various cell lines with DNA damage repair deficiencies as indicated in the table. LC50 and LC90 values (pM) are given for each cell line. FIG. 28 (Table 2) shows the effect of MK7-206 on various cell lines with DNA damage repair deficiencies as indicated in the table. LC50 and LC90 values (nM) are given for the cell lines tested. FIG. 29 (Table 3) shows the effect of (−)-lomaiviticin A on various cell lines with DNA damage repair deficiencies as indicated in the table as a function of percent survival at 4 and 10 pM of LA. FIG. 30 (Table 4) shows the effect of MK7-206 on various cell lines with DNA damage repair deficiencies as indicated in the table as a function of percent survival at 20 and 60 nM of MK7-206.

DETAILED DESCRIPTION OF THE INVENTION

Figure 1:
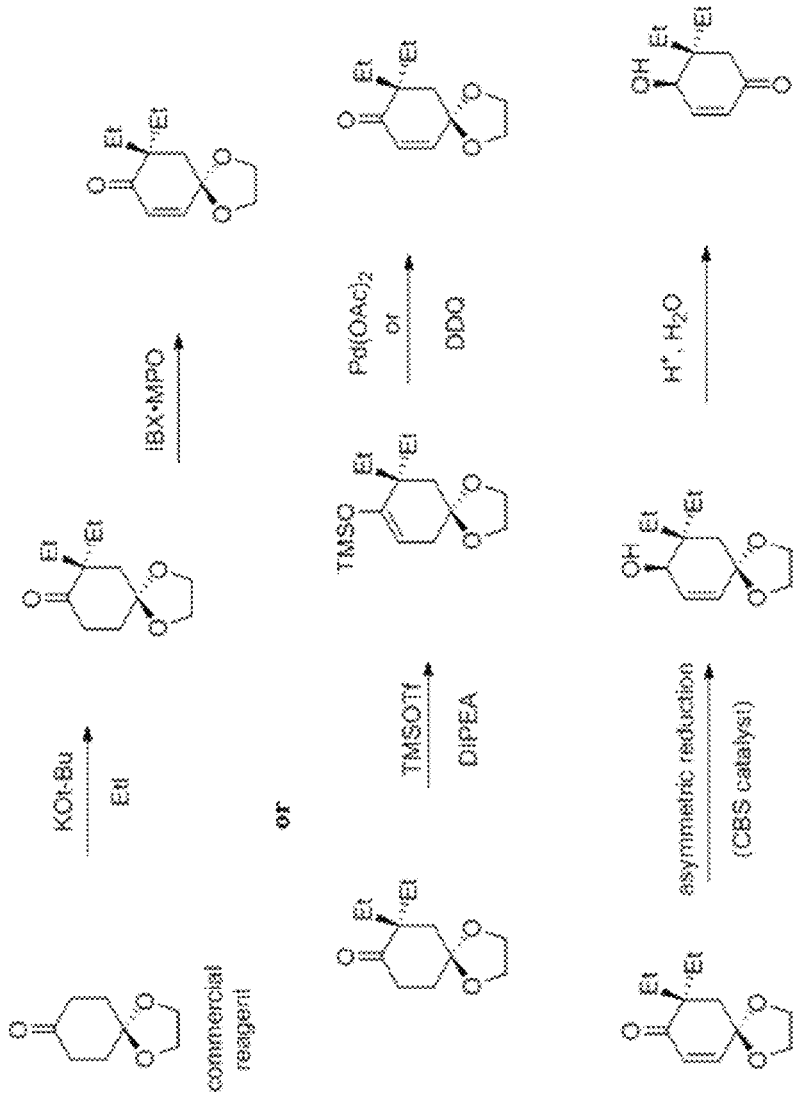
FIGS. 1-14 show the chemical synthetic schemes of a number of compounds and/or precursors of compounds according to the present invention.

The following terms are used to describe the present invention. In instances where a term is not specifically defined herein, that term is given an art-recognized meaning by those of ordinary skill applying that term in context to its use in describing the present invention.

The term "compound", as used herein, unless otherwise indicated, refers to any specific chemical compound disclosed herein and includes tautomers, regioisomers, geometric isomers, and where applicable, optical isomers (enantiomers) thereof, as well as pharmaceutically acceptable salts and derivatives (including prodrug forms) thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds (at least about 70% enantiomerically enriched, preferably greater than 90% enantiomerically enriched and in certain preferred embodiments, substantially pure or pure enantiomers where the compound is more than 98-99% or more enantiomerically enriched). The term also refers, in context, to prodrug forms of compounds which have been modified to facilitate the administration and delivery of compounds to a site of activity. It is noted that in describing the present compounds, numerous substituents, linkers and connector molecules and variables associated with same, among others, are described. It is understood by those of ordinary skill that molecules which are described herein are stable compounds as generally described hereunder and variables are chosen (oftent in combination) which promote the stability of the compound described.

The term "patient" or "subject" is used throughout the specification within context to describe an animal, generally a mammal and preferably a human, to whom treatment, including prophylactic treatment (prophylaxis), with the compositions according to the present invention is provided. For treatment of those infections, conditions or disease states which are specific for a specific animal such as a human patient or a patient of a particular gender, such as a human male or female patient, the term patient refers to that specific animal or that gender. Compounds according to the present invention are useful for the treatment, inhibition or prophylaxis ("reducing the likelihood") of cancer, including metastatic and recurrent cancer.

The term "effective" is used herein, unless otherwise indicated, to describe an amount of a compound or composition (most often a chimeric compound which include dimeric or polymeric cleavage/intercalating agents which are covalently linked to a cancer cell targeting moiety) which, in context, is used to produce or effect an intended result, whether that result relates to the inhibition of cancer, including metastatic cancer or the treatment of a subject for secondary conditions, disease states or manifestations of cancer as otherwise described herein. This term subsumes all other effective amount or effective concentration terms (including the term "therapeutically effective") which are otherwise described in the present application.

The terms "treat", "treating", and "treatment", etc., as used herein, refer to any action providing a benefit to a patient at risk for cancer, including the metastasis or recurrence of cancer, including improvement in the condition through lessening or suppression of at least one symptom, inhibition of cancer growth, reduction in cancer cells or tissue, prevention or delay in progression of metastasis of the cancer, prevention or delay in the onset of disease states or conditions which occur secondary to cancer or remission or cure of the cancer, among others. Treatment, as used herein, encompasses both prophylactic and therapeutic treatment. The term "prophylactic" when used, means to reduce the likelihood of an occurrence or the severity of an occurrence within the context of the treatment of cancer, including cancer metastasis as otherwise described hereinabove.

The term "tumor" is used to describe a malignant or benign growth or tumefacent.

The term "neoplasia" refers to the uncontrolled and progressive multiplication of tumor cells, under conditions that would not elicit, or would cause cessation of, multiplication of normal cells. Neoplasia results in a "neoplasm", which is defined herein to mean any new and abnormal growth, particularly a new growth of tissue, in which the growth of cells is uncontrolled and progressive. Thus, neoplasia includes "cancer", which herein refers to a proliferation of tumor cells having the unique trait of loss of normal controls, resulting in unregulated growth, lack of differentiation, local tissue invasion, and/or metastasis. The cancer may be "naïve", metastatic or recurrent and includes drug resistant and multiple drug resistant cancers, all of which may be treated using compounds according to the present invention.

As used herein, neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms are distinguished from benign neoplasms in that the former show a greater degree of anaplasia, or loss of differentiation and orientation of cells, and have the properties of invasion and metastasis. Examples of neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine/endometrial cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas, which may be treated by one or more compounds according to the present invention. See, (Beers and Berkow (eds.), The Merck Manual of Diagnosis and Therapy, 17.sup.th ed. (Whitehouse Station, N.J.: Merck Research Laboratories, 1999) 973-74, 976, 986, 988, 991.

The term "DNA repair factor" refers to cellular mechanisms of DNA repair which make therapy against cancer especially when a DNA damaging agent (such as those of the present invention) is utilized. In certain cancers, the DNA repair factors are upregulated and in others the DNA repair factors are downregulated, thus making cancer therapy with a DNA damaging agent such as a cleavage and/or intercalating agent particularly effective. These susceptible deficient cancer cells are referred to in the art as DNA repair response deficient (DDR-deficient) cells. Thus, DDR-deficient cancers in which at least one DNA repair factor, including KU80, pten, BRCA2, DNApk, ATM, PALB2 and/or RAD51 paralogs are down regulated, make excellent targets of therapy using compounds according to the present invention. In addition, the present compounds exhibit excellent inhibition/cytotoxicity against hypoxic cancer cells, making anti-tumor therapy effective using compounds according to the present invention. Compounds according to the present invention may be combined with one or more of the various traditional anticancer agents which are otherwise disclosed herein and may optionally combine radiation therapy to produce an intended effect of inhibiting or treating the cancer (except in the case of hypoxic cells, which tend to be resistant to radiation therapy). In addition, cancer therapy may also include an inhibitor of one or more of the DNA repair factors (KU80, pten, BRCA2, DNApk, ATM, PALB2 and/or RAD51) such as siRNA which inhibits expression of the DNA factor, thus providing particularly effective targets of compounds according to the present invention.

Because of the activity of the present compounds and their ability to target various cancer cells along with a general mechanism of antiproliferation based upon a polynucleotide cleavage (breakage) and/or intercalation mechanism, the present invention has general applicability treating virtually any cancer in any tissue, thus the compounds, compositions and methods of the present invention are generally applicable to the treatment of cancer. Given that the various targets of the present compounds are found on cancer cells, including the neovasculature of most cancer cells (especially with respect to PSMA binding moieties), the compounds in the present invention may also serve as an antiangiogenic therapy for other cancer types in addition to the antiproliferative activity of the compounds in general.

In certain particular aspects of the present invention, the cancer which is treated is metastatic cancer. Metastatic cancer may be found in virtually all tissues of a cancer patient in late stages of the disease, including the lymph system/nodes (lymphoma), in bones, in bladder tissue, in kidney tissue, liver tissue and in virtually any tissue, including brain (brain cancer/tumor). Thus, the present invention is generally applicable and may be used to treat any cancer in any tissue, regardless of etiology. In other instances, the cancer which is treated, including prophylactically treated, is a recurrent cancer, which often recurs after an initial remission. The present compounds also may be used to reduce the likelihood of a cancer recurring and for treating a cancer which has recurred.

The term "intercalating moiety which is an analog of lomaiviticin A", (ILM) or "intercalating moiety" (IM) is used to described that portion of a chimeric compound (which compound includes at least one intercalating moiety (IM) to which is bound at least one cancer cell targeting moiety (CCTM) most often through a linker molecule (L), which is usually a cleavable linker) which causes damage to a polynucleotide (especially DNA) through a cleavage (causing polynucleotide breaks) and/or an intercalation mechanism resulting in polynucleotide damage and cell death. Intercalating moieties for inclusion in chimeric compounds according to the present invention are those compounds which are bound to L-CCTM groups as otherwise described herein. These intercalating moieties may be monomeric or dimeric as set forth herein.

The term "cancer cell targeting moiety", "CCTM" or "cell targeting moiety" is used to describe that portion of a chimeric compound according to the present invention which comprises at least one moiety which is capable of selectively binding to a cancer cell. CCTM groups for including in chimeric compounds according to the present invention include small molecules which bind to folate receptors (folate receptor binding moiety), antibody-type CCTMs such as monoclonal antibodies (especially a humanized monoclonal antibody) such as herceptin or antibody fragments (FAB), including single chain variable fragment (scFv) antibodies which bind to cancer cells, a PSMA binding moiety or a YSA peptide (which binds to Ephrin A2 (EphA2), as otherwise described herein.

The term "folate receptor binding moiety" (FRBM) or (FM) is used to describe a folate moiety which binds to cancer cells selectively and is used in the present invention to target folate receptors on cancer cells which are often overexpressed or hyperexpressed on cancer cells compared to normal cells.

The folate receptor, given its selective heightened expression on cancer cells compared to normal cells represents an excellent selective target to bind compounds according to the present invention to cancer cells for uptake into cells where the intercalating moiety may exhibit its antiproliferative activity, resulting in cancer cell death. Folate receptor I is often overexpressed in numerous numerous cancer cells including ovarian, breast, uterine, cervical, renal, lung, colorectal and brain cancer cells, thus making it an important targeting site for compounds according to the present invention.

Folate receptor binding moieties for use in the present invention include the following chemical structures:

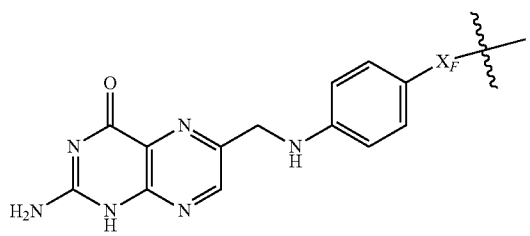

where $X_F$ is C(O), S(O), S(O)$_2$, CR$_F$R$_F$, O, S or N—R$_F$, where R$_F$ is H or a $C_1$-$C_3$ alkyl (preferably H).

The term "prostate specific membrane antigen" or "PSMA" according to the chemical structure is directed to a cancer cell targeting moiety that binds to prostate specific membrane antigen (PSMA) which is frequently overexpressed or hyperexpressed in cancer cells. PSMA, although found on prostate cancer cells, including metastatic prostate cancer cells, are also found on virtually all other cancer cells and may be used to selectively target compounds according to the present invention to cancer cells. A number of metastatic and recurrent cancers also hyperexpress PSMA compared to naïve cancers and PSMA may represent a particularly useful binding site for metastatic and/or recurrent cancers.

PSMA binding moieties include moieties according to the chemical structure:

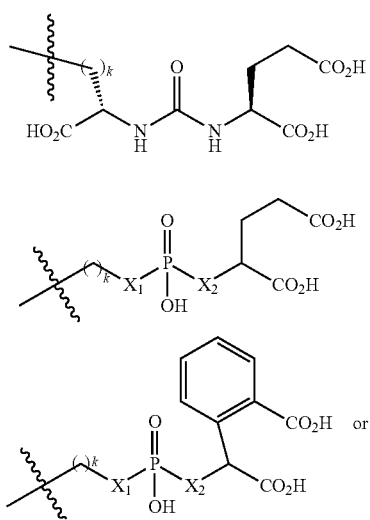

-continued

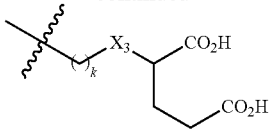

Where $X_1$ and $X_2$ are each independently $CH_2$, O, NH or S; $X_3$ is O, $CH_2$, $NR^1$, S(O), S(O)$_2$, —S(O)$_2$O, —OS(O)$_2$, or OS(O)$_2$O;

$R^1$ is H, a $C_1$-$C_3$ alkyl group, or a —C(O)($C_1$-$C_3$) group;

k is an integer from 0 to 20, 8 to 12, 1 to 15, 1 to 10, 1 to 8, 1 to 6, 1, 2, 3, 4, 5 or 6;

or a salt or enantiomer thereof.

A preferred PSMA binding group (CCTM) for use in the present invention is the group

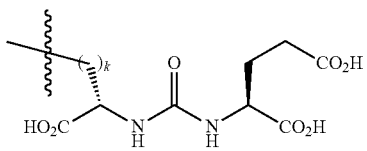

Where k is 2, 3 or 4, preferably 3. This CCTM group, as well as the others, optionally has an amine group or other functional group at the distill end of the alkylene group (k) such that k is formed from, for example, a lysine amino acid, such that the amine group or other functional group may participate in further reactions to form a linker, a connector group [CON], a multifunctional group [MULTICON] or may be linked directly to an (ILM) as otherwise described herein.

The term "antibody", also referred to an immunoglobulin (Ig), is a protein, which is Y-shaped and produced by B-cells that the immune system uses to identify and neutralize foreign objects in the body, such as pathogens, including viruses, bacteria and cancer cells, which the immune system recognizes as objects to the immune system. As used herein, antibody includes, but is not limited to, monoclonal antibodies. The following disclosure from U.S. Patent Application Document No. 20100284921, the entire contents of which are hereby incorporated by reference, exemplifies techniques that are useful in making antibodies which may be modified and employed in chimeric compounds of the instant invention.

Pursuant to its use in the present invention, the antibody is preferably a chimeric antibody. For human use, the antibody is preferably a humanized chimeric antibody. [A]n anti-target-structure antibody . . . may be monovalent, divalent or polyvalent in order to achieve target structure binding. Monovalent immunoglobulins are dimers (HL) formed of a hybrid heavy chain associated through disulfide bridges with a hybrid light chain. Divalent immunoglobulins are tetramers (H2L2) formed of two dimers associated through at least one disulfide bridge.

As discussed above, the term antibody for use in the present invention includes compounds which exhibit binding characteristics comparable to those of the antibodies, and include, for example, hybridized and single chain antibodies, as well as fragments thereof. Methods of producing such compounds are disclosed in PCT Application Nos. WO 1993/21319 and WO 1989/09622. These compounds include polypeptides with amino acid sequences substantially the same as the amino acid sequence of the variable or hypervariable regions of the antibodies raised against targets on cancer cells pursuant to the practice of the present invention. These may be readily modified to link these CCTMs to the (ILM), thus forming chimeric compounds hereunder.

Compounds according to the present invention which serve to bind to target cancer cells include fragments of antibodies (FAB) that have the same, or substantially the same, binding characteristics to those of the whole antibody. Such fragments may contain one or both Fab fragments or the F(ab')$_2$ fragment. Preferably the antibody fragments contain all six complement determining regions of the whole antibody, although fragments containing fewer than all of such regions, such as three, four or five complement determining regions, are also functional. The functional equivalents are members of the IgG immunoglobulin class and subclasses thereof, but may be or may combine any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Preferred constant regions are gamma 1 (IgG1), gamma 2 (IgG2 and IgG), gamma 3 (IgG3) and gamma 4 (IgG4). The light chain constant region can be of the kappa or lambda type.

In another approach, the monoclonal antibodies may be advantageously cleaved by proteolytic enzymes to generate fragments retaining the target structure binding site. For example, proteolytic treatment of IgG antibodies with papain at neutral pH generates two identical so-called "Fab" fragments, each containing one intact light chain disulfide-bonded to a fragment of the heavy chain (Fc). Each Fab fragment contains one antigen-combining site. The remaining portion of the IgG molecule is a dimer known as "Fc". Similarly, pepsin cleavage at pH 4 results in the so-called F(ab')2 fragment.

Single chain antibodies or Fv fragments are polypeptides that consist of the variable region of the heavy chain of the antibody linked to the variable region of the light chain, with or without an interconnecting linker. Thus, the Fv comprises an antibody combining site. Hybrid antibodies also may be employed as CMTs in the chimeric compounds according to the present invention. Hybrid antibodies have constant regions derived substantially or exclusively from human antibody constant regions and variable regions derived substantially or exclusively from the sequence of the variable region of a monoclonal antibody from each stable hybridoma.

Methods for preparation of fragments of antibodies (e.g. for preparing an antibody or an antigen binding fragment thereof having specific binding affinity for a cancer cell target are readily known to those skilled in the art. See, for example, Goding, "Monoclonal Antibodies Principles and Practice", Academic Press (1983), p. 119-123. Fragments of the monoclonal antibodies containing the antigen binding site, such as Fab and F(ab')2 fragments, may be preferred in therapeutic applications, owing to their reduced immunogenicity. Such fragments are less immunogenic than the intact antibody, which contains the immunogenic Fc portion. Hence, as used herein, the term "antibody" includes intact antibody molecules and fragments thereof that retain antigen binding ability.

When the antibody used in the methods used in the practice of the invention is a monoclonal antibody, the antibody is generated using any known monoclonal antibody preparation procedures such as those described, for example, in Harlow et al. (supra) and in Tuszynski et al. (Blood 1988, 72:109-115). Generally, monoclonal antibodies directed against a desired antigen are generated from mice immunized with the antigen using standard procedures as referenced herein. Monoclonal antibodies directed against full length or fragments of target structure may be prepared using the techniques described in Harlow et al. (supra).

Chimeric animal-human monoclonal antibodies may be prepared by conventional recombinant DNA and gene transfection techniques well known in the art. The variable region genes of a mouse antibody-producing myeloma cell line of known antigen-binding specificity are joined with human immunoglobulin constant region genes. When such gene constructs are transfected into mouse myeloma cells, the antibodies produced are largely human but contain antigen-binding specificities generated in mice. As demonstrated by Morrison et al., 1984, Proc. Natl. Acad. Sci. USA 81:6851-6855, both chimeric heavy chain V region exon (VH)-human heavy chain C region genes and chimeric mouse light chain V region exon (VK)-human K light chain gene constructs may be expressed when transfected into mouse myeloma cell lines. When both chimeric heavy and light chain genes are transfected into the same myeloma cell, an intact H2L2 chimeric antibody is produced. The methodology for producing such chimeric antibodies by combining genomic clones of V and C region genes is described in the above-mentioned paper of Morrison et al., and by Boulianne et al. (Nature 1984, 312:642-646). Also see Tan et al. (J. Immunol. 1985, 135: 3564-3567) for a description of high level expression from a human heavy chain promotor of a human-mouse chimeric K chain after transfection of mouse myeloma cells. As an alternative to combining genomic DNA, cDNA clones of the relevant V and C regions may be combined for production of chimeric antibodies, as described by Whitte et al. (Protein Eng. 1987, 1:499-505) and Liu et al. (Proc. Natl. Acad. Sci. USA 1987, 84:3439-3443). For examples of the preparation of chimeric antibodies, see the following U.S. Pat. Nos. 5,292,867; 5,091,313; 5,204,244; 5,202,238; and 5,169,939. The entire disclosures of these patents, and the publications mentioned in the preceding paragraph, are incorporated herein by reference. Any of these recombinant techniques are available for production of rodent/human chimeric monoclonal antibodies against target structures.

When antibodies other than human antibodies are modified for incorporation into chimeric compounds pursuant to the present invention, it may be necessary to reduce the immunogenicity of the murine antibody. To further reduce the immunogenicity of murine antibodies, "humanized" antibodies have been constructed in which only the minimum necessary parts of the mouse antibody, the complementarity-determining regions (CDRs), are combined with human V region frameworks and human C regions (Jones et al., 1986, Nature 321:522-525; Verhoeyen et al., 1988, Science 239:1534-1536; Hale et al., 1988, Lancet 2:1394-1399; Queen et al., 1989, Proc. Natl. Acad. Sci. USA 86:10029-10033). The entire disclosures of the aforementioned papers are incorporated herein by reference. This technique results in the reduction of the xenogeneic elements in the humanized antibody to a minimum. Rodent antigen binding sites are built directly into human antibodies by transplanting only the antigen binding site, rather than the entire variable domain, from a rodent antibody. This technique is available for production of chimeric rodent/human anti-target structure antibodies of reduced human immunogenicity."

The term antibody fragment or "FAB" is used to describe a fragment of an antibody which substantially maintains the same binding characteristics of the whole antibody, but eliminates other chemical features of the antibody which may complicate administration and produce untoward immunogenic responses in a patient.

The term "single-chain antibody variable fragment") or "scFv" is used to describe an artificial construct that links the sequences encoding the $V_H$ and $V_L$ domains of an antibody into a single polypeptide chain and lacks the rest of the antibody molecule. Because the antigen-binding site of an antibody is formed in a cavity at the interface between $V_H$ and $V_L$ domains, the scFv preserves the antigen binding activity of the intact antibody molecule. Normally the $V_H$ and $V_L$ domains are parts of different polypeptide chains (the heavy and light chains, respectively), but in the scFv they are joined into a single polypeptide that can be fused genetically to other proteins, for example, proteins on cancer cells to be targeted. These scFvs may form the basis of effective CCTMs on chimeric compounds according to the present invention.

The term "linker" (designated as "L" or "(L) in compounds according to the present invention) is used to describe a chemical moiety which, when present in chimeric molecules according to the present invention, covalently binds a (ILM) group to a (CCTM) group. The linker group may be cleavable or noncleavable depending on the function of the CCTM group. In general, antibody or antibody related (CCTM) groups described above are generally, but not exclusively linked to a (ILM) group through a cleavable linker group. Other CCTMs often are linked to (ILM) groups through a non-cleavable linker group.

Typical cleavable linker groups (L), which may be represented as ($L_C$), for use in the present invention are represented by any chemical structure which is compatible with the chemistry of the chimeric compounds and their administration to a patient and readily cleave in or on a cell in which the chimeric molecule is introduced. In general, the cleavable linker for use in compounds according to the present invention is at least one chemical moiety, more often at least two chemical moieties in length to upwards of 100 or more moieties in length. These linkers are presented in detail hereinbelow. Often, one or more cleavable linker groups may be linked to one or more non-cleavable (non-labile) linker groups either directly or through a connector group (CON) or multiconnector group (MULTICON) as otherwise described herein. These form a complex linker.

Cleavable or labile linkers ($L_C$) allow the [ILM] moiety to be cleaved from the (CCTM) in compounds according to the present invention order to provide a maximal effect in the cell, by allowing the ILM to be cleaved from the CCTM after the compound targets the cancer cell, facilitating entry of the ILM into the cell which causes cleavage/breakage and/or intercalation of the cell's DNA, causing cytotoxicity and cell death. These labile linkers include hydrolytically labile (acid labile) linkers, reductively labile linkers (principally disulfide linkers which are reductively cleaved by intracellular glutathione or other disulfide reducing agent) and enzymatically labile linkers (protease substrates).

In certain embodiments according to the present invention, the cleavable linker $L_C$ is a disulfide wherein one of the sulfurs in the disulfide group is provided by a cysteinyl residue alone or as an oligopeptide ranging from about 1 to about 10 amino acid units in length, often 1, 2 or 3 amino acid units in length. In certain embodiments the oligopeptide is represented by a glutamyl cysteinyl dipeptide (with the amide formed between the sidechain carboxylic acid of the glutamic acid and the amine of the cysteinyl residue), a glycinyl cysteinyl dipeptide, an alaninyl cysteinyl dipeptide or a lysinyl cystinyl dipeptide. The dipeptide may be linked (mated) with another dipeptide of similar or different structure each having a cysteinyl residue linked to the cysteinyl residue of the other dipeptide, or the dipeptide may be linked with a mercaptide such as an alkyl mercaptide (which is further substituted with a group which can further link the cleavable linker to another group, such as a non-cleavable (non-labile) linker an (ILM) group or a (CCTM) group or a connector group, etc.

In other embodiments the cleavable linker group ($L_C$) is an oligopeptide (containing a disulfide group as described above) or other linker which contains an ester group which may readily cleaved. For example, a linker may consistent of a dipeptide such as a glutamyl cysteinyl group which provides a disulfide link to a linker (such as a alkylene group or polyethylene glycol group) which can form a connector molecule (such as a difunctional triazole CON group or a MULTICON group) as otherwise described herein, or alternatively bind directly to an ILM group or a CCTM group.

Cleavable or labile linkers ($L_C$) may comprise a group represented by the chemical structures:

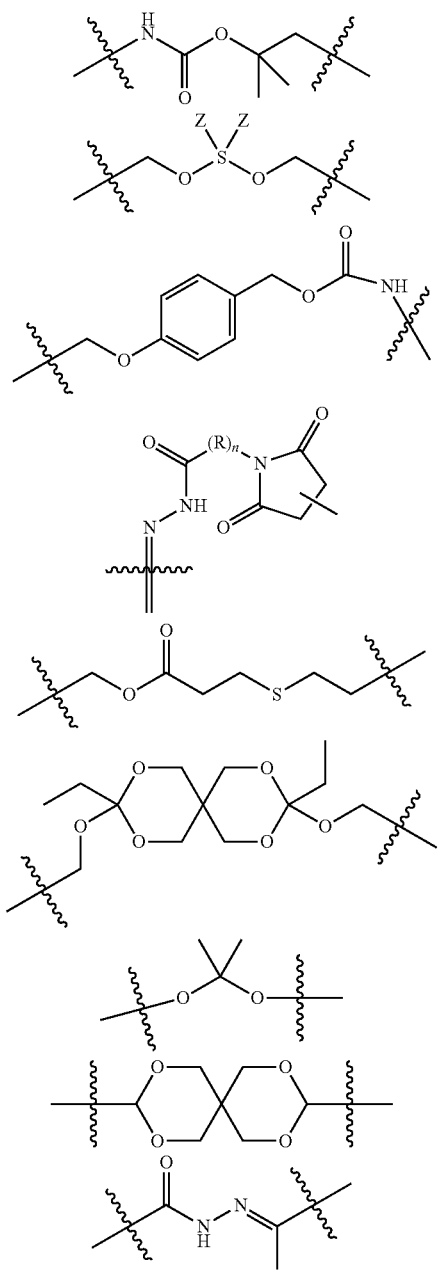

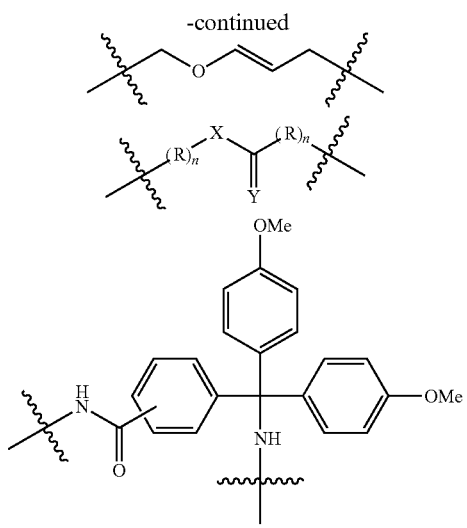

where R is an ethylene glycol group, a methylene group or an amino acid, preferably an ethylene glycol group or an amino acid and n in this labile linker is from 0 to 10, often from 1 to 6, or 1 to 3 and where points of attachment (as indicated) are to other portions of the cleavable or labile linker ($L_C$), a difunctional connector moiety (CON), a non-cleavable (non-labile) linker ($L_N$), or a multifunctional connector molecule [MULTICON], through which an [ILM] functional group and a [CCTM] functional group are linked as otherwise described herein;

X is O, N—$R^{AL}$ or S;

$R^{AL}$ is H or a $C_1$-$C_3$ alkyl group (often H or Me, most often H);

Y is O or S and

Z=Me, Et, iPr, tBu, Ph, each of which may be optionally substituted with one or more halogen groups (especially from three up to five Fs, preferably no more than three Fs) and where said Ph group may be further optionally substituted with a $C_1$-$C_3$ alkyl group (which itself may be substituted with up to three halogens, preferably F) or OMe.

Exemplary reductively cleaved moieties (by glutathione, other reductive species within the cell) include moieties according to the chemical formula:

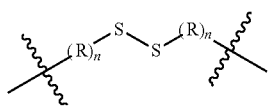

Where R is independently an ethylene glycol group, a methylene group or an amino acid where at least one amino acid (that which provides one of the sulfurs in the disulfide group) is a cysteinyl group (often, (R)n is a glutamyl cysteinyl or lysinyl cysteinyl dipeptide) and n in this labile linker is from 0 to 10, often from 1 to 6, or 1, 2 or 3 and where points of attachment (as indicated) are to other portions of the labile linker [LL], a difunctional connector molecule or group (CON), a non-labile linker (NLL) or a multifunctional connector group molecule [MULTICON] as otherwise described herein.

Exemplary enzymatically cleaved labile linkers include those according to the chemical structure:

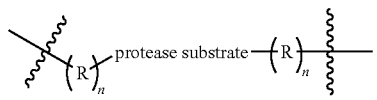

Where the protease (cathepsin) substrate is a a peptide containing from 2 to 50 amino acid units or more, often 2 to 25 amino acid units, 2 to 15 amino acid units, 2 to 10 amino acid units, 2 to 6 amino acids, 2 to 4 amino acids, 2, 3 or 4. Often, the protease substrate, above contains, comprises, consists essentially of or consists of the following peptides the point of attachment being at the distal ends of the peptide:
- -Gly-Phe-Leu-Gly-;
- -Ala-Leu-Ala-Leu;
- -Phe-Arg-;
- -Phe-Lys-;
- -Val-Cit- (valine-citrillune)
- -Val-Lys-
- -Val-Ala- and where R (above) is an ethylene glycol group, or a methylene group and n is from 0 to 10, often from 1 to 6, or 1 to 3 and where points of attachment (as indicated) are joined to other portions of the labile linker, a difunctional connector group or molecule (CON), a non-labile linker (NLL), a virus invasion cell binding moiety (VICB) or a cytotoxic moiety (CYT) as otherwise described herein Other enzyme labile linkers are the beta-glucosidase labile linkers according to the chemical structure:

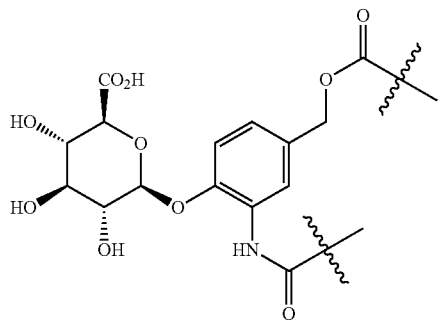 [SMILES: *C(=O)Nc1cc(COC(*)=O)ccc1O[C@@H]1O[C@H](C(=O)O)[C@@H](O)[C@H](O)[C@H]1O]

Where the points of attachment are joined to other portions of the labile linker, a difunctional connector moiety (CON), a non-labile linker (NLL) or a multifunctional connector group or molecule [MULTICON] as otherwise described herein.

In each of the above labile linkers, at the point of attachment in each group, the labile linker may be further linked to a non-labile linker as otherwise described herein, preferably a (poly)ethylene glycol group of from 1 to 12 glycol units (often 2 to 8 glycol units or 4 to 6 units) or an alkylene chain from 1 to 20 methylene units, often 1 to 10 methylene units, often 1 to 8 methylene units, more often 1 to 6 methylene unit, often 2 to 4 methylene units.

Preferred non-labile linkers include, for example, (poly) ethylene glycol linkers ranging in length from 2 to about 100 ethylene glycol units, preferably about 2 to 10 ethylene glycol units, about 2 to about 25, about 2 to about 15, about 2 to about 14, about 4 to about 10 units. In other preferred embodiments, the non-cleavable linker ($L_N$) is a polyethylene-co-polypropylene (PEG/PPG block copolymer) linker ranging from 2 to about 100, about 2 to about 25, about 2 to about 15, about 2 to about 14, about 2 to about 10, about 4 to about 10, combined ethylene glycol and propylene glycol units.

(Poly)alkylene chains as otherwise described herein are also preferred $L_N$ for use in the present invention. When present, these have 1 to about 100 units, often about 2 to 10 units, about 2 to about 25, about 2 to about 15, about 2 to about 14, about 4 to about 10 units. $L_N$ for use in the present invention may also contain one or more connector CON moieties as otherwise described herein which chemically connect separate (two or more) $L_N$ portions, the entire portion being labeled $L_N$. In addition, a non-cleavable linker $L_N$ may be linked through at least one connector moiety CON (as described in greater detail herein) to a cleavable linker $L_C$ in order to provide a linker moiety.

In certain preferred embodiments, the non-cleavable linker ($L_N$) is represented by the following exemplary structures (note that the $L_N$ may contain one ore more CON moieties as discussed above):

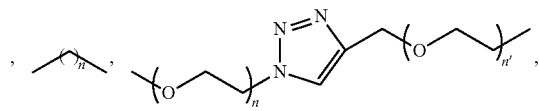

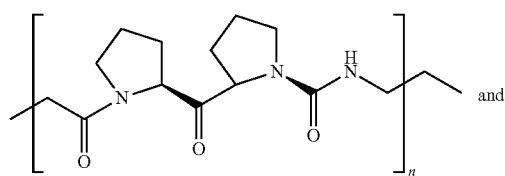

POLYPROLINE LINKER

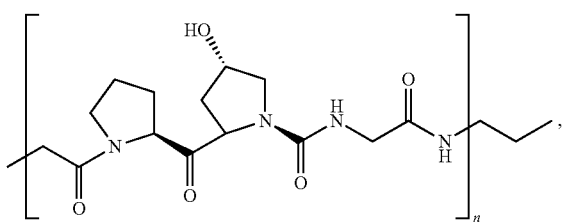

COLLAGEN LINKER among numerous others, as described herein.

where n and n' are each independently 0 to 100, preferably 1 to 100, more preferably about 2 to about 20, about 2 to about 10, about 4 to about 10, about 4 to about 8.

The linker group $L_N$ may also be a linker according to the chemical formula:

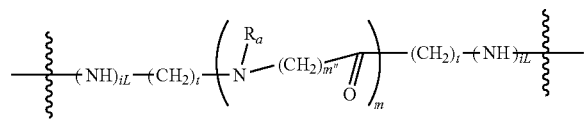

where $R_a$ is H or a $C_1$-$C_3$ alkyl, preferably $CH_3$, most often H;
m is an integer from 1 to 12, often 1, 2, 3, 4, 5, or 6;
m" is an integer 1, 2, 3, 4, 5, or 6, often 6;
t is 0, 1, 2, 3, 4, 5, or 6; and
iL is 0 or 1, often 1; or a linker according to the structure:

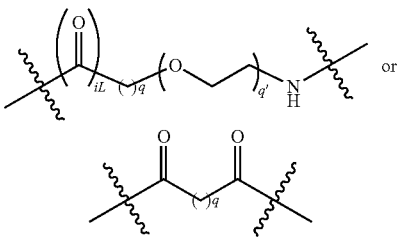

Where q is an integer from 0-12, preferably 1, 2, 3, 4, 5 or 6;
q' is 1 to 12, often 1, 2, 3, 4, 5 or 6 and
iL is 0 or 1, preferably 1.

The two above linkers may be linked together to provide further linkers which are often used in compounds according to the present invention:

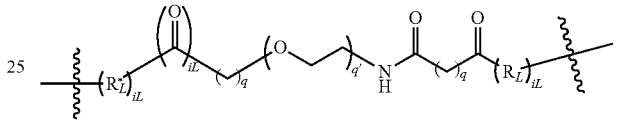

Where q is an integer from 0-12, preferably 0, 1, 2, 3, 4, 5 or 6;
q' is 1 to 12, often 1, 2, 3, 4, 5 or 6;
iL is 0 or 1; and
$R_L$ is an amino acid or an oligopeptide (which term includes a dipeptide) as otherwise described herein, especially including lysine, dilysine, or glycinelysine.

Another linker according to the present invention includes a linker based upon succinimide according to the chemical formula:

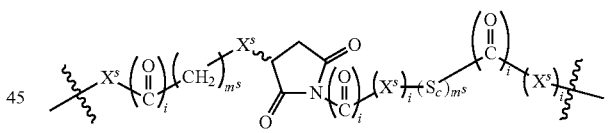

where each $X^S$ is independently a bond, S, O or N—$R^S$, preferably S;
$R^S$ is H or $C_{1-3}$ alkyl, preferably H;
$S_c$ is $CH_2$, $CH_2O$; or $CH_2CH_2O$;
i is 0 or 1; and
$m^S$ is 0, 1, 2, 3, 4, 5, 6, 7, 8, 9 or 10 (preferably 1-5).

In certain additional embodiments, the linker group $L_N$ is an amino acid, a dipeptide or an oligopeptide containing from 1 to 12, preferably 1 to 6 amino acid monomers or more. In certain embodiments, the oligopeptide is a dipeptide and the dipeptide is a dilysine or a glycinelysine dipeptide. When lysine is used as an amino acid in an oligopeptide linker, the sidechain alkylene amine may be used to link other linker groups or other components in the molecule. The dipeptide or oligopeptide may be considered a cleavable linker or non-cleavable depending upon the nature of the peptide.

In certain additional embodiments, as discussed above, the linker group $L_N$ is a group

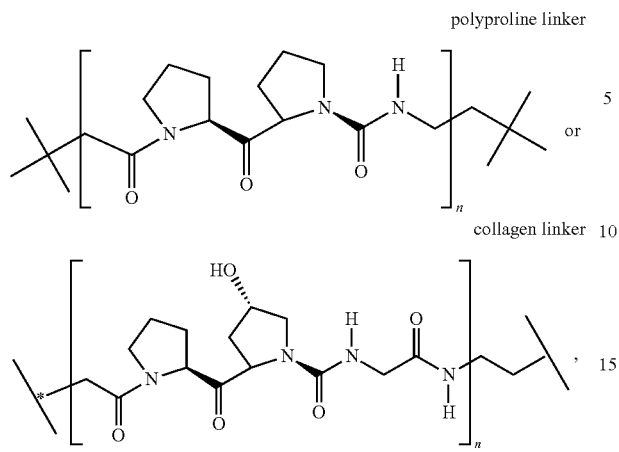

polyproline linker collagen linker a group

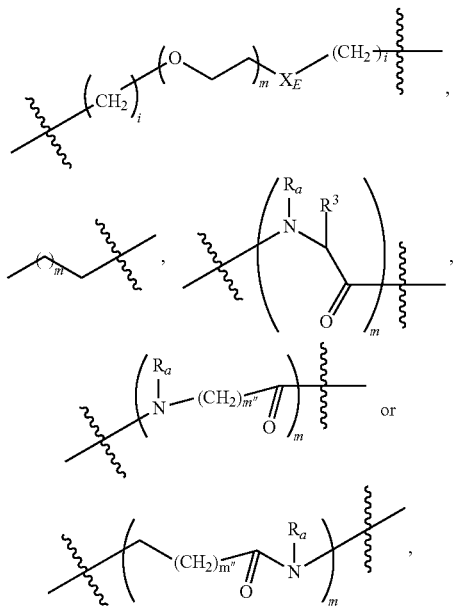

or a polypropylene glycol or polypropylene-co-polyethylene glycol linker having between 1 and 100 glycol units (1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 52 and 50, 3 and 45);

Where $R_a$ is H, $C_1$-$C_3$ alkyl or alkanol or forms a cyclic ring with $R^3$ (proline) and $R^3$ is a side chain derived of an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline ($R^3$ forms a cyclic ring with $R_a$ and the adjacent nitrogen group to form a pyrrolidine group), serine (methanol), threonine (ethanol, 1-hydroxyethane), tryptophan (methyleneindole), tyrosine (methylene phenol) or valine (isopropyl);

$X_E$ is a bond, O, N—$R_{NA}$, or S;
$R_{NA}$ is H or $C_1$-$C_3$ alkyl, preferably H;
i is an integer from 0 to 6 (0, 1, 2, 3, 4, 5, or 6);
m" is an integer from 0 to 25, preferably 1 to 10, 1 to 8, 1, 2, 3, 4, 5, or 6;
m is an integer from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; and
n is an integer from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; or
$L_{N'}$ may also be a linker according to the chemical formula:

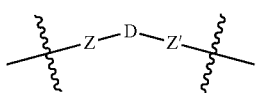

Where Z and Z' are each independently a bond, —$(CH_2)_i$—O, —$(CH_2)_i$—S, —$(CH_2)_i$—N—R,

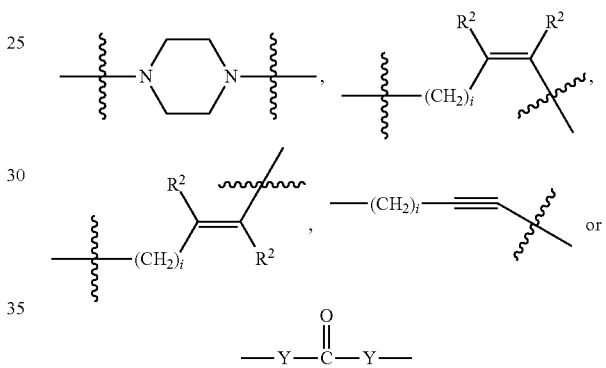

—Y—C(=O)—Y— wherein said —$(CH_2)_i$ group, if present in Z or Z', is bonded to [ILT], [CCMT], or an optional difunctional connector group [CON], if present;
Each R is independently H, or a $C_1$-$C_3$ alkyl or alkanol group;
Each $R^2$ is independently H or a $C_1$-$C_3$ alkyl group;
Each Y is independently a bond, O, S or N—R;
Each i is independently 0 to 100, 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;
D is

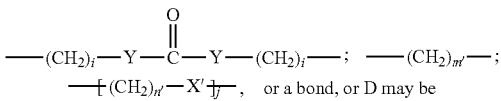

, or a bond, or D may be

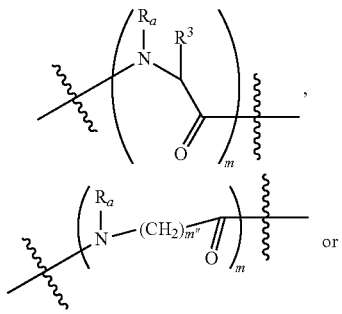

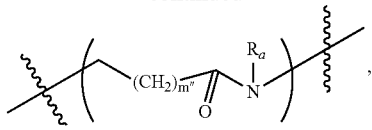

or a polypropylene glycol or polypropylene-co-polyethylene glycol linker having between 1 and 100 glycol units (1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 52 and 50, 3 and 45); with the proviso that Z, Z' and D are not each simultaneously bonds;

j is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

m (within this context) is an integer from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; and n (within this context) is an integer from about 1 to 100, about 1 to 75, about 1 to 60, about 1 to 50, about 1 to 45, about 1 to 35, about 1 to 25, about 1 to 20, about 1 to 15, 2 to 10, about 4 to 12, about 5 to 10, about 4 to 6, about 1 to 8, about 1 to 6, about 1 to 5, about 1 to 4, about 1 to 3, etc.).

m' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

m" is an integer between 0 to 25, preferably 1 to 10, 1 to 8, 0, 1, 2, 3, 4, 5, or 6;

n' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

$X^1$ is O, S or N—R;

R is as described above;

$R_a$ is H, $C_1$-$C_3$ alkyl or alkanol or forms a cyclic ring with $R^3$ (proline) and $R^3$ is a side chain derived of an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline ($R^3$ forms a cyclic ring with $R_a$ and the adjacent nitrogen group to form a pyrrolidine group), serine (methanol), threonine (ethanol, 1-hydroxyethane), tryptophan (methyleneindole), tyrosine (methylene phenol) or valine (isopropyl).

It is noted that each of the linkers (both cleavable and non-cleavable linkers) identified in the present application may be further linked with connector molecules/moieties [CON] molecules/moieties, [ILM] groups and [CCMT] groups through amide groups (which include alkylene groups on either or both sides of the amide group containing one to five methylene units), keto groups (which include alkylene keto groups containing one to five methylene units on either or both sides of the keto group), amine groups (which include alkylene amine groups containing one to five methylene units on either or both sides of the amine group), urethane groups (which include alkylene groups containing one to five methylene units on either or both sides of the urethane moiety), alkylene groups (containing from 1 to 5 methylene units), urea groups (which include alkylene groups containing one to five methylene units on either or both sides of the urethane moiety) amino acids or other moieties compatible with the linker chemistry in order to link components of the molecules. It is noted that in the case of polyethylene glycol and polypeptide linkers, the use of an additional group (eg, alkylene amine or other group as described above) or a second linker group may be useful for joining the linker to another component of the molecule, including a [CON] group.

Additionally, more than one linker group identified herein may be linked together to form a linker group as otherwise used in the present compounds, consistent with the stability of the linker chemistries. These extended linkers are often, though not exclusively linked through [CON] connecting groups as otherwise described herein.

The term "difunctional connnector group" or [CON] is used to describe a difunctional group which connects two (or more) portions of a linker group to extend the length of the linker group. In certain embodiments, a linker group is reacted with or forms a [CON] group with another linker group to form an extended linker group. The reaction product of these groups results in an identifiable connector group [CON] which is distinguishable from the linker group as otherwise described herein. It is further noted that there may be some overlap between the description of the difunctional connector group and the linker group, especially with respect to more common connector groups such as amide groups, oxygen (ether), sulfur (thioether) or amine linkages, urea or carbonate —OC(O)O— groups as otherwise described herein. It is noted that a difunctional connector molecule [CON] used hereunder is often connected to two parts of a linker group which binds [ILM] to [CCMT]. Alternatively, a [CON] group may be directly linked to a [IBT] group or more often, a [CBT] group, as well as a [MULTICON] group as described herein.

Common difunctional connector groups [CON] which are used in the present invention, principally to link one end of a linker to another end of a linker to provide a longer linker include the following chemical groups:

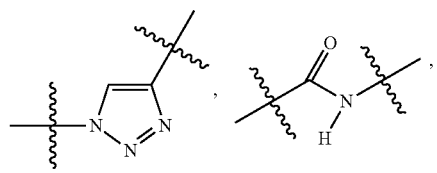

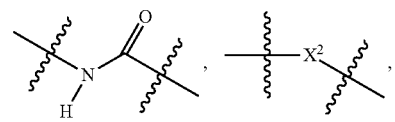

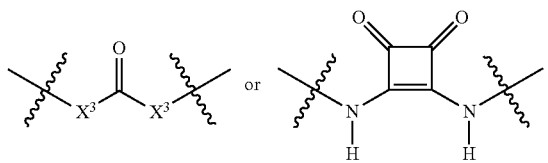

Where $X^2$ is O, S, $NR^4$, S(O), $S(O)_2$, —$S(O)_2O$, —$OS(O)_2$, or $OS(O)_2O$;

$X^3$ is O, S, $NR^4$; and $R^4$ is H, a $C_1$-$C_3$ alkyl or alkanol group, or a —C(O)($C_1$-$C_3$) group.

In certain embodiments, [CON] is a

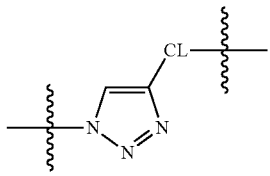

group;
where CL is

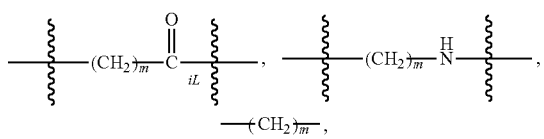

an amide, keto group, urethane or urea;
m in CL is an integer from 0 to 12, often 0, 1,2,3,4,5 or 6;
and iL is 0 or 1, often 1;

In certain embodiments, this [CON] group is often linked through the amine of the triazole to a cleavable or non-cleavable linker.

The term "multifunctional connector", symbolized by [MULTICON], is used to describe a chemical group or molecule which is optionally included in chimeric compounds according to the present invention which link at least one or more linker groups (which may be cleavable or non-cleavable), difunctional connector groups (CON), (ILM) groups or (CCTM) groups as otherwise described herein. The connector group is the resulting moiety which forms from the facile condensation of at least three separate chemical fragments which contain reactive groups which can provide connector groups as otherwise described to produce chimeric compounds according to the present invention. It is noted that a multifunctional connector moiety or molecule [MULTICON] is readily distinguishable from a linker in that the multifunctional connector is the result of a specific chemistry which is used to provide chimeric compounds according to the present invention.

Connecting moieties in the present invention include at least one multifunctional moiety or molecule [MULTICON] which contains three or more functional groups which may be used to covalently bind (preferably, through a linker) to at least one [ILM] group (preferably more than one) and at least one [CCTM] group (preferably more than one), thus linking each of these functional groups into a single compound. Multifunctional connector groups for use in the present invention include moities which have at least three or more functional groups which can bind to linkers to which are bound [ILM] and/or [CCTM] groups in order to provide compounds which contain at least one [ILM] and [CCTM] groups, but preferably more than one of each of these groups pursuant to the present invention. These multifunctional connector moieties may also bind to other multifunctional connector molecules in order to create compounds containing a number of [ILM] and [CCMT] groups as defined herein.

Multifunctional connector molecules [MULTICON] comprise any molecule or moiety which contains at least three groups which may be linked to [ILM], [CCMT] and/or linkers (non-labile linkers or labile linkers) and/or other connector groups (including difunctional and multifunctional connector groups) and often comprise five or six-membered aryl or heteroaryl groups (especially six-membered ring groups) exemplified by multifunctional, especially trifunctional or tetrafunctional aryl or heteroaryl groups, including phenyl, pyridyl, pyrimidinyl, 1,3,5-triazinyl, 1,2,3-triazinyl, 1,2,4-triazinyl groups, each of which is substituted with at least 3 and up to 6 functional groups. These functional groups may be derived from nucleophilic or electrophilic groups on the multifunctional connector molecule precursor (the multifunctional connector molecule which forms the [MULTICON] moiety in final compounds according to the present invention) which are condensed onto linker groups (each of which contains, for example an [ILM] group or a [CCTM] group) which contains a group which can be linked to the [MULTICON] moiety. [MULTICON] groups which are used in the present invention preferably include substituted phenyl, pyridyl, pyrimidinyl and 1,3,5-triazinyl, 1,2,3-triazinyl, 1,2,4-triazinyl groups, and other groups of multifunctionality especially including groups according to the chemical structure:

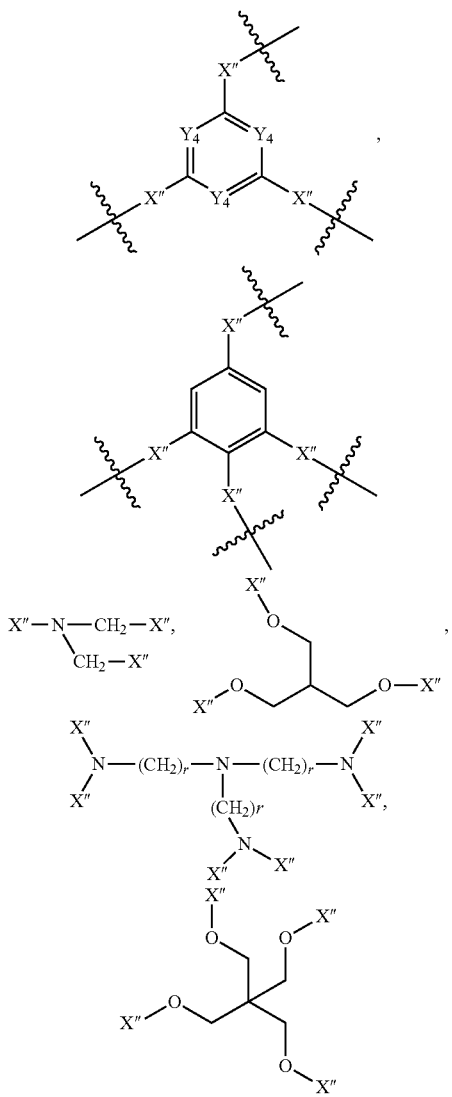

-continued

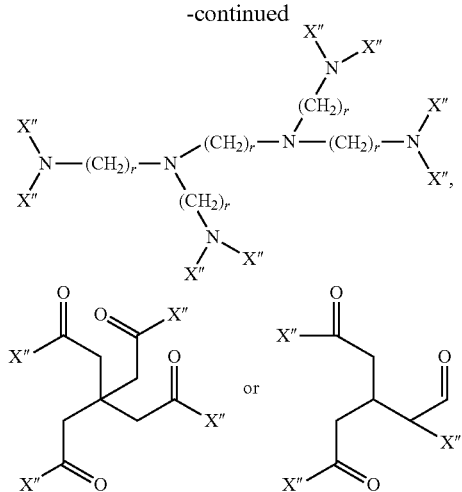

where $Y_4$ is C—H or N; and
Each X" is independently derived from an electrophilic or nucleophilic group, preferably $(CH_2)_n$—O, $(CH_2)_n$—$NR^{CON}$, $(CH_2)_n$—S, $(CH_2)_n$— or $(CH_2)_n$, C=O;
the substituent $R^{CON}$ is H or a $C_1$-$C_3$ alkyl, preferably H or $CH_3$,
n" is 0, 1, 2 or 3 and
r is an integer from 1-12, often 1, 2, 3, 4, 5 or 6.

The term "pharmaceutically acceptable salt" or "salt" is used throughout the specification to describe a salt form of one or more of the compositions herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts may be preferred as neutralization salts of carboxylic acids and free acid phosphate containing compositions according to the present invention. The term "salt" shall mean any salt consistent with the use of the compounds according to the present invention. In the case where the compounds are used in pharmaceutical indications, including the treatment of prostate cancer, including metastatic prostate cancer, the term "salt" shall mean a pharmaceutically acceptable salt, consistent with the use of the compounds as pharmaceutical agents.

The term "coadministration" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time. Chimeric antibody-recruiting compounds according to the present invention may be administered with one or more additional anti-cancer agents or other agents which are used to treat or ameliorate the symptoms of cancer, especially prostate cancer, including metastatic prostate cancer.

The term "anticancer agent" or "additional anticancer agent" refers to a compound other than the chimeric compounds according to the present invention which may be used in combination with a compound according to the present invention for the treatment of cancer. Exemplary anticancer agents which may be coadministered in combination with one or more chimeric compounds according to the present invention include, for example, antimetabolites, inhibitors of topoisomerase I and II, alkylating agents and microtubule inhibitors (e.g., taxol), among others. Exemplary anticancer compounds for use in the present invention may include everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab (Arzerra), zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258,); 3-[5-(methylsulfonylpiperadinemethyl)-indolylj-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro- Azgly-NH$_2$ acetate [$C_{59}H_{84}N_{18}Oi_4$-$(C_2H_4O_2)$x where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafamib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, among others.

In addition to anticancer agents, a number of other agents may be coadministered with chimeric compounds according to the present invention in the treatment of cancer. These include active agents, minerals, vitamins and nutritional supplements which have shown some efficacy in inhibiting cancer tissue or its growth or are otherwise useful in the treatment of cancer. For example, one or more of dietary selenium, vitamin E, lycopene, soy foods, curcumin (turmeric), vitamin D, green tea, omega-3 fatty acids and phytoestrogens, including beta-sitosterol, may be utilized in combination with the present compounds to treat cancer.

Without not being limited by way of theory, anticancer compounds according to the present invention which contain a cancer cell targeting moiety (CCTM) and intercalating moiety (ILM) selectively bind to cancer cells and through that binding, facilitate the introduction of the (ILM) moiety into the cancer cell selectively, where, the compound, inside the cell or during transport into the cancer cell, the cleavable linker is cleaved from the cancer cell targeting moiety, providing an agent for intercalating and/or damaging through breakage the cancer cell's DNA and causing cell death.

Pharmaceutical compositions comprising combinations of an effective amount of at least one compound disclosed herein, often a difunctional chimeric compound (containing at least one ILM and at least one CCTM) according to the present invention, and one or more of the compounds as otherwise described herein, all in effective amounts, in combination with a pharmaceutically effective amount of a carrier, additive or excipient, represents a further aspect of the present invention. These may be used in combination with at least one additional, optional anticancer agent as otherwise disclosed herein.

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir, among others. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally (including via intubation through the mouth or nose into the stomach), intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially to treat skin cancers, psoriasis or other diseases which occur in or on the skin. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one additional non-antibody attracting compound which may be used to treat cancer, prostate cancer or metastatic prostate cancer or a secondary effect or condition thereof.

Methods of treating patients or subjects in need for a particular disease state or condition as otherwise described herein, especially cancer, comprise administration of an effective amount of a pharmaceutical composition comprising therapeutic amounts of one or more of the novel compounds described herein and optionally at least one additional bioactive (e.g. anti-cancer) agent according to the present invention. The amount of active ingredient(s) used in the methods of treatment of the instant invention that may be combined with the carrier materials to produce a single dosage form will vary depending upon the host treated, the particular mode of administration. For example, the compositions could be formulated so that a therapeutically effective dose of between about 0.01, 0.1, 1, 5, 10, 15, 20, 25, 30, 35, 40, 45, 50, 55, 60, 65, 70, 75, 80, 85, 90 or 100 mg/kg of patient/day or in some embodiments, greater than 100, 110, 120, 130, 140, 150, 160, 170, 180, 190 or 200 mg/kg of the novel compounds can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject (e.g. a male human) suffering from cancer can be treated by administering to the patient (subject) an effective amount of a chimeric compound according to the present invention including pharmaceutically acceptable salts, solvates or polymorphs, thereof optionally in a pharmaceutically acceptable carrier or diluent, either alone, or in combination with other known anticancer or pharmaceutical agents, preferably agents which can assist in treating cancer, including metastatic cancer or ameliorate the secondary effects and conditions associated with cancer. This treatment can also be administered in conjunction with other conventional cancer therapies, such as radiation treatment or surgery.

The present compounds, alone or in combination with other agents as described herein, can be administered by any appropriate route, for example, orally, parenterally, intravenously, intradermally, subcutaneously, or topically, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from about 0.01-3% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as other anticancer agents, antibiotics, antifungals, antiinflammatories, or antiviral compounds. In certain preferred aspects of the invention, one or more chimeric antibody-recruiting compound according to the present invention is coadministered with another anticancer agent and/or another bioactive agent, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methylparabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled and/or sustained release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions or cholestosomes may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Rationale for Design of Compounds

The first goal in constructing compounds according to the present invention is to design an appropriate bifunctional/chimeric molecule capable of binding to a cancer cell and deposit at least a portion of the molecule (the ILM moiety) into the cell to intercalate and/or damage through breakage DNA and produce cell death. It is our finding that linking a cancer cell targeting moiety (CCTM) to an intercalating moiety as otherwise described herein would provide a targeting approach to delivering the intercalating moiety to a cancer cell selectively. To that end, a variety of CCTMs were covalently connected to ILM moieties through linkers as otherwise described herein to provide chimeric compounds which bind cancer cells and deposit ILM moieties (either detached from or linked to the CCTM) into a cell to promote the death of the cell. Thus, the present compounds rely on linking an ILM moiety as otherwise disclosed herein which has polynucleotide intercalating and/or cleavage (cell death) capability with a CCTM which targets sites on cancer cells (often receptors or other polypeptides) to selectively bind the chimeric compound to the cancer cells for uptake (either the entire chimeric molecule or at least the ILM portion of the molecule upon cleavage of the ILM from the chimeric molecule).

Chemical Synthesis

In order to synthesize compounds according to the present invention, chemical synthetic steps which are well known in the art used. These often are simple condensation reactions. Chimeric molecules according to the present invention are synthesized by condensing a linker molecule onto a functional group of an ILM group or a CCTM group and thereafter, either extending the linker which is covalently linked to the ILM group (or CCTM) to a CCTM (or ILM group). Various approaches may be used. We provide exemplary chemistry for providing numerous compounds according to the present invention.

As set forth in attached FIG. 1, the protected cyclohexanone compound is first dialkylated in a first step using a common procedure and the dialkyl derivative is then subjected to IBX•MPO according to the procedure of Nicolaou, et al. *Angew. Chem., Int. Ed.* 2002, 41, 996 to introduce a double bond into the cyclohexane moiety as depicted in FIG. 1. Alternatively the dialkylated intermediate is subject to silanation (using TMSOTf followed by DIPEA) to produce the silane protected intermediate which is reduced using palladium diacetate or DDQ according to the methods of Ito, et al., *Org. Chem.* 1978, 43, 1011 (Pd catalyst) or Ryu, et al. *Tetrahedron Lett.* 1978, 19, 3455 (DDQ). The dialkylated cyclohexenone derivative is then asymmetrically reduced to provide the corresponding protected alcohol which can be deprotected using standard acid hydrolysis to provide the dialkylated cyclohexenone alcohol as depicted in FIG. 1. The cyclohexenone alcohol can be used to provide an ILM group to which is bonded a carbohydrate moiety as set forth in attached FIG. 3.

Figure 2:
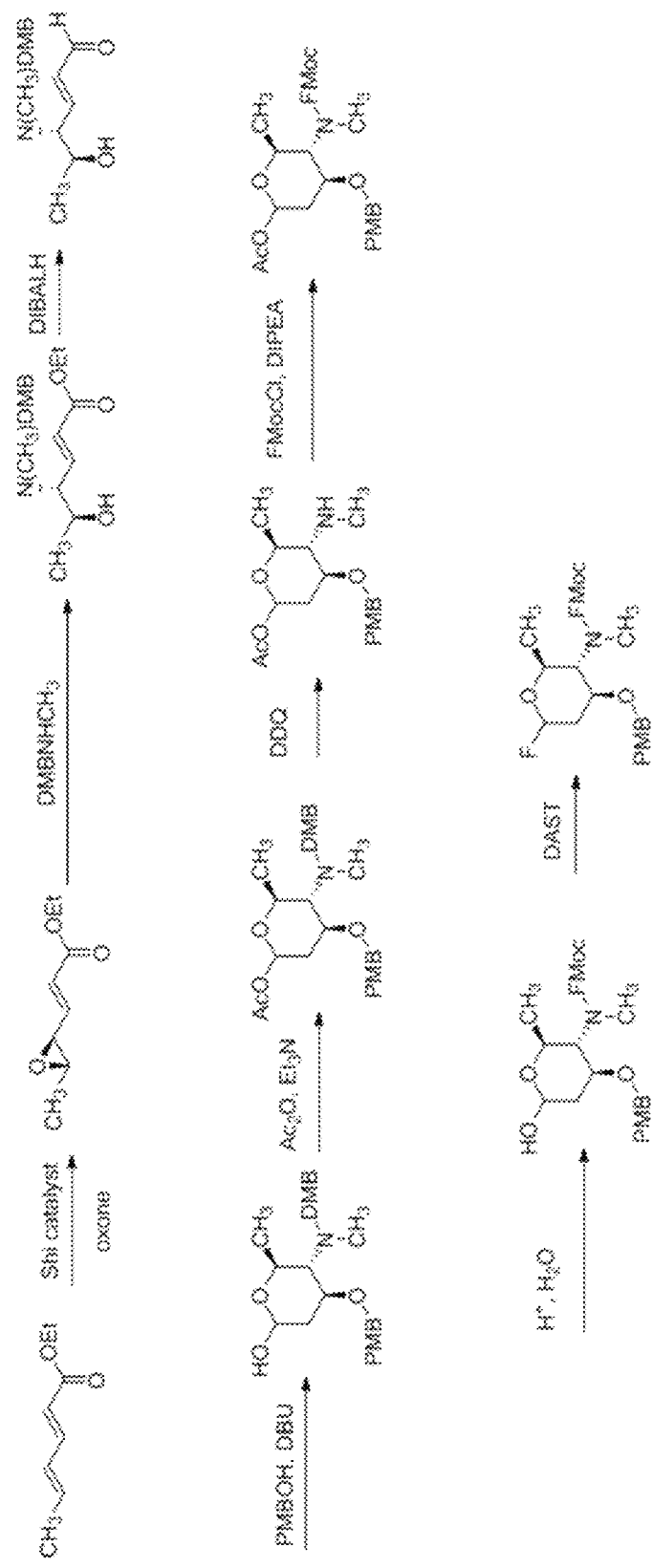
Figure 6:
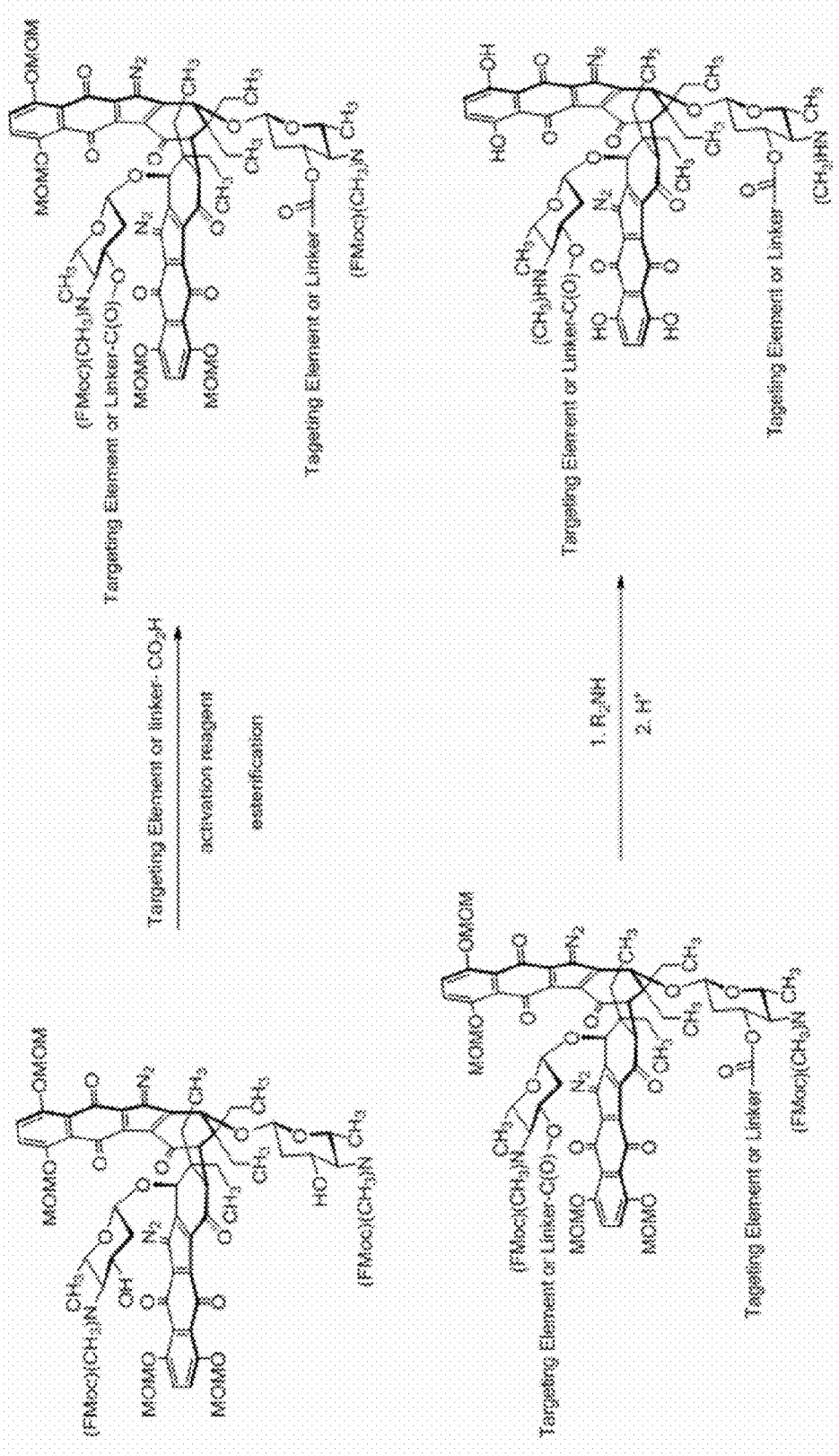

FIG. 2 shows an exemplary synthesis of a carbohydrate used on the ILM group of certain embodiments according to the present invention. As depicted in FIG. 2, the carbohydrate is formed from the starting material which is first subjected to a Shi catalyst and oxone to form the resulting epoxide following the procedures of Frohn, et al., *J Org. Chem.* 1998, 63, 2948. The epoxide is then reacted with $DMBNHCH_3$ (Dimethoxybenzyl methylamine) to form the corresponding aminated alcohol by analogy following the procedure of Gholap, et al., *Org. Lett.* 2009, 11, 4322. Procedures in that same reference were used to reduce the ester to the corresponding aldehyde, which was cyclized using PMBOH and DBU pursuant to the procedures of Gholap, et al., supra, to form the aminated carbohydrate derivative. That carbohydrate was readily acetylated and the DMB group removed in DDQ, and the FMoc protecting group was used to protect the free amine as indicated. The acetyl group was removed using standard hydrolysis conditions and the fluorine was substituted for the hydroxyl group using DAST (diethylaminosulfur trifluoride) following the procedure of Posner and Haines, *Tetrahedron Lett.* 1985, 26, 5 to form the final fluorinated intermediate of FIG. 2 which was further condensed with the dialkylated cyclohexenone alcohol of FIG. 1 to provide ILM groups with attached carbohydrate which can be further derivatized pursuant to the chemical scheme presented in attached FIGS. 4 and 6 to provide final chimeric compounds according to the present invention.

Figure 3:
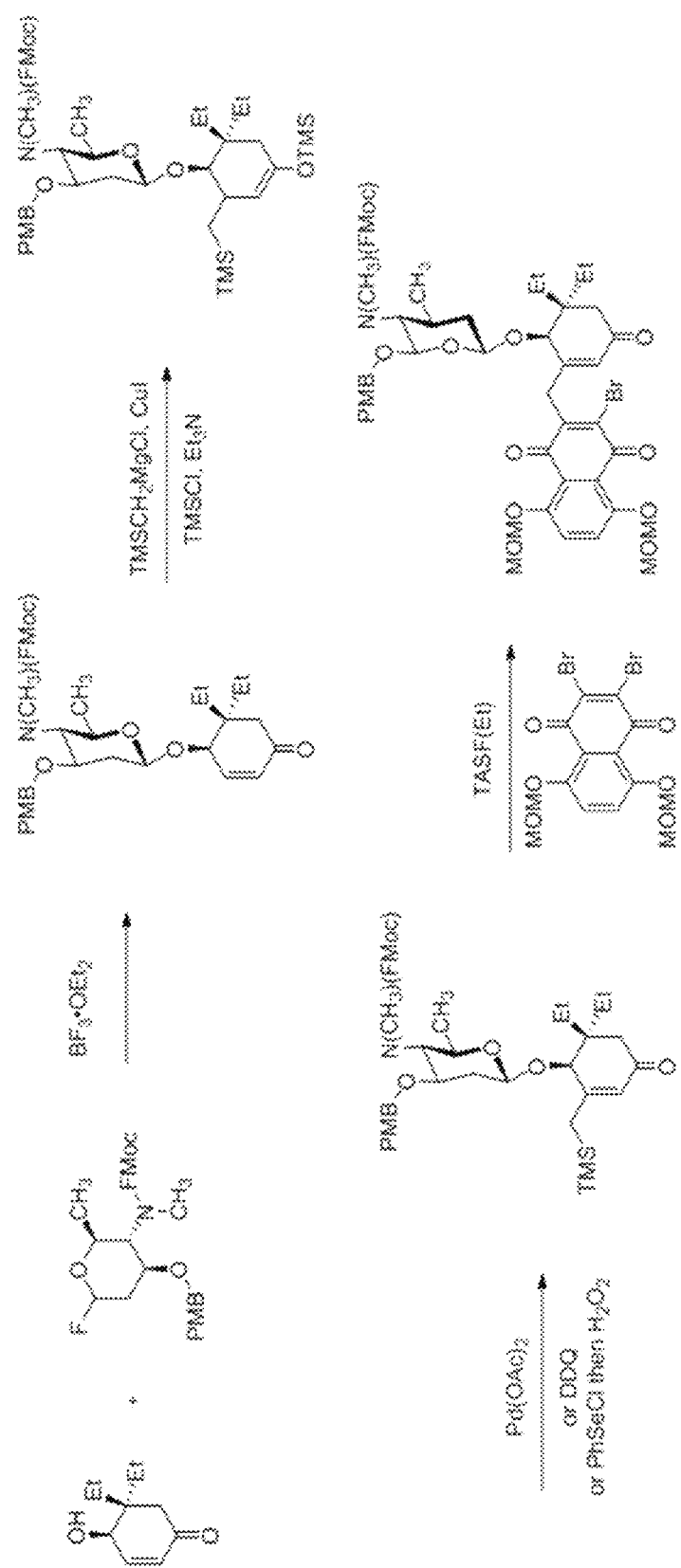

Pursuant to the chemical scheme set forth in attached FIG. 3, the dialkylated cyclohexenone alcohol is condensed with the fluorinated carbohydrate of FIG. 2 using the Lewis acid $BF_3.OEt_2$ by analogy to the procedure of Gholap, et al., supra, to form the cyclohexenone alcohol-linked carbohydrate which is alkylated and protected as indicated by analogy pursuant to the procedures of Woo, et al., *J. Am. Chem. Soc.* 2010, 132, 2540; Herzon, et al., J. Am. Chem. Soc. 2011, 133, 7260 and Woo, et al., *J. Am. Chem. Soc.* 2012, 134, 17262. That intermediate is then reduced to form the alkylated enone in $Pd(OAc)_2$ or DDQ or PhSeCl, followed by hydrogen peroxide pursuant to the procedures of Ito, et al., *J. Org. Chem.* 1978, 43, 1011 (Pd); Murai, et al., *Tetrahedron Lett.* 1978, 19, 3455 (DDQ); or Reich, et al., *J. Am. Chem. Soc.* 1975, 97, 5434 (PhSeCl), which is then reacted with the dibrominated fused cyclic analog in TASF(Et) to condense the fused cyclic ring onto the cyclohexenone moiety forming a methylene bridge. See Woo, et al., Herzon, et al., and Woo, et al, supra.

Figure 4:
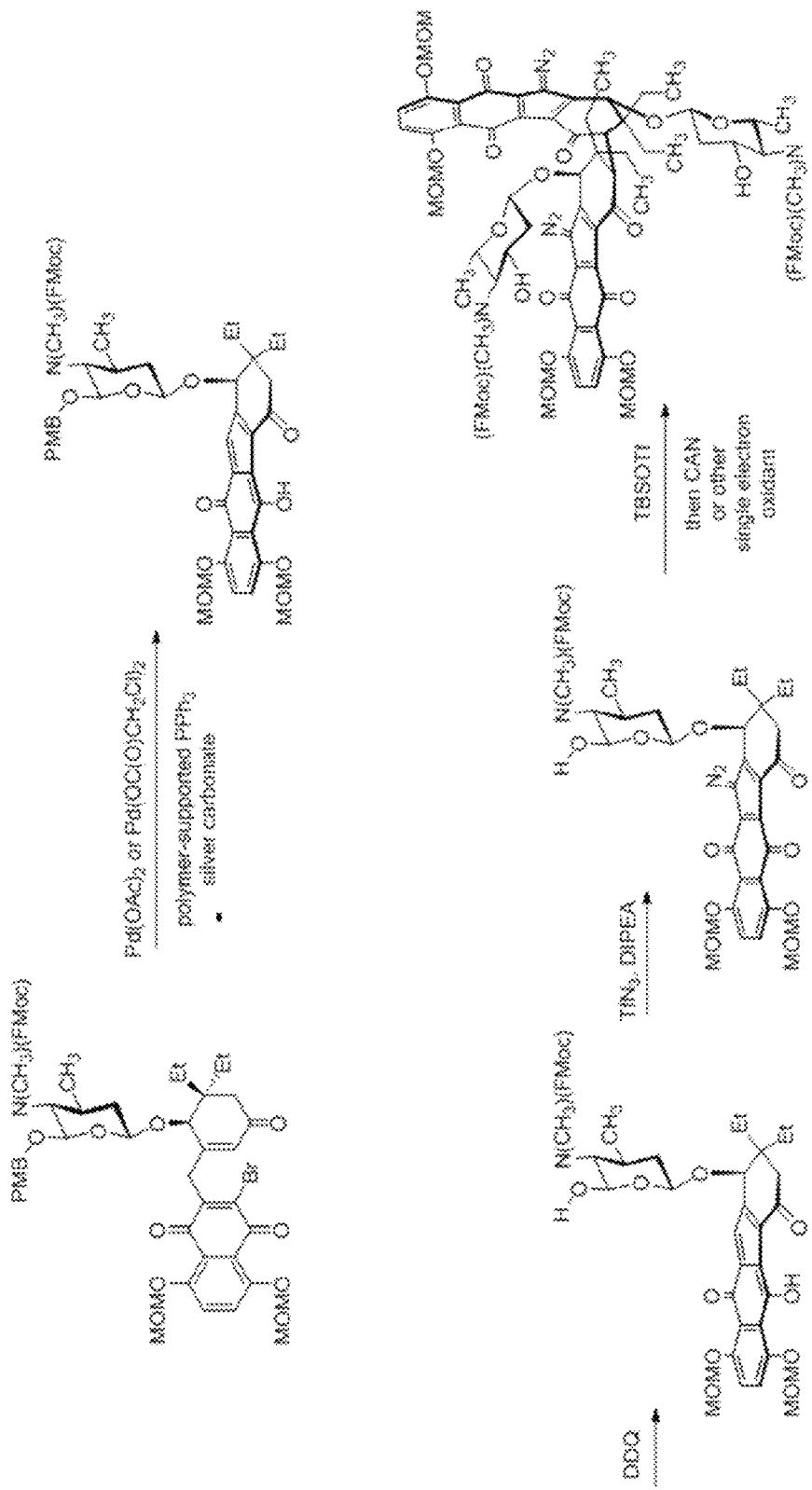

Pursuant to the chemical scheme set forth in attached FIG. 4, the fused cyclic ring and cyclohexenone moiety (to which is attached a carbohydrate as indicated in FIG. 4) is cyclized to a four membered ring using $Pd(OAc)_2$ or $Pd(OC(O)CH_2Cl_2$ and $PPH_3$ (polymer supported) and silver carbonate, pursuant to the approach presented in Woo, et al., Herzon, et al., and Woo, et al, supra. That substituted four ring intermediate is then subjected to DDQ to remove the PMB group provide the free hydroxyl intermediate which is subjected to $TfN_3$ and DIPEA pursuant to the described method of Woo, et al., Herzon, et al., and Woo, et al, supra. to introduce a diazo group on the five membered ring as shown in FIG. 4, which is subsequently dimerized in the presence of TBSOTf followed by CAN or other single electron oxidant pursuant to the method described in Herzon, et al., *J. Am. Chem. Soc.* 2011, 133, 7260 and Woo, *J. Am. Chem. Soc.* 2012, 134, 17262 (also cited above) to produce the dimerized protected intermediate as set forth in FIG. 4. As set forth in the chemical scheme of FIG. 6, the dimerized protected intermediate can be linked to a linker-CCTM group by pre-preparing a linker-CCTM intermediate which contains a functional group (such as a carboxylic acid, or other electrophilic group) which can be condensed onto the free hydroxyl groups of the dimerized ILM group. As set forth in FIG. 6, the dimerized protected intermediate containing two free hydroxyl groups are esterified with a targeting element-linker which contains a carboxylate group (an alternative of an isocyanate would produce a more stable urethane group and other more stable groups are also contemplated, for example a urea group, among others) to provide the esterified protected intermediate which links two CCTM groups as indicated. The esterified protected intermediate may be deprotected using standard procedures well known in the art to provide the final chimeric molecule which contains a dimerized ILM group and two CCTM groups.

Figure 5:
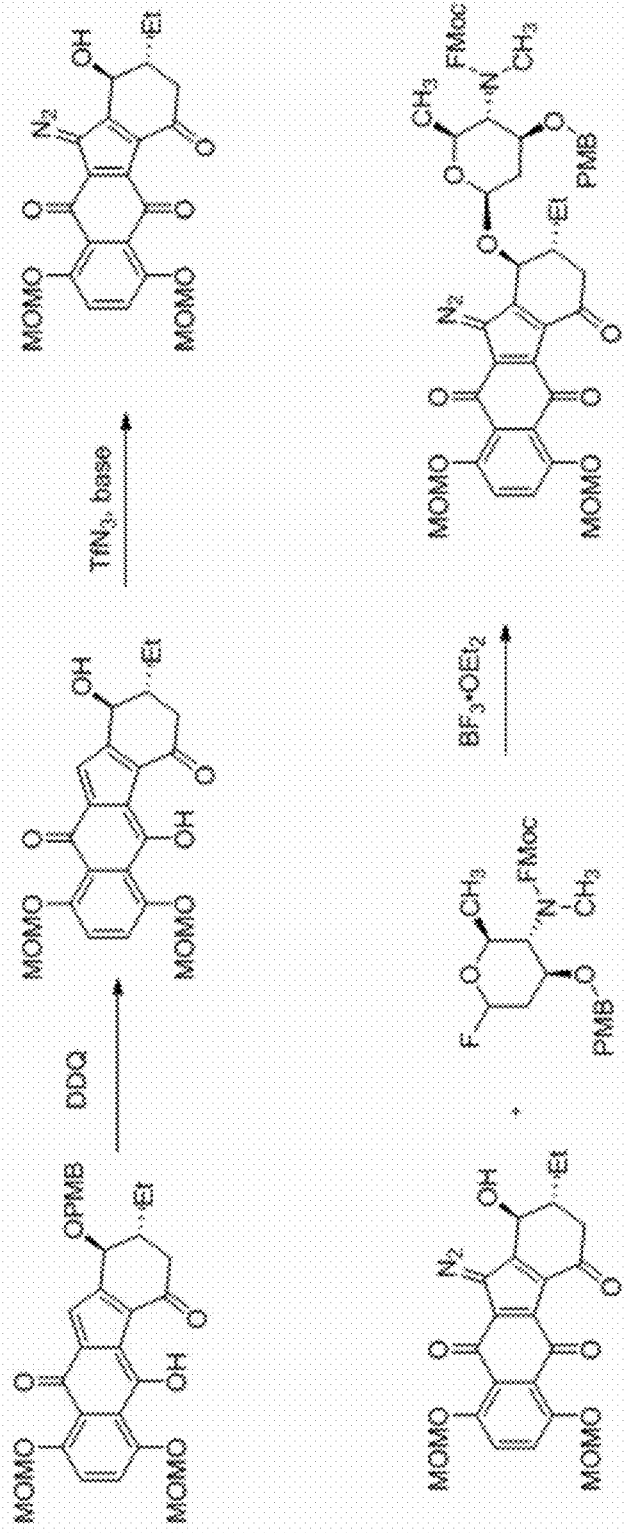
Figure 7:
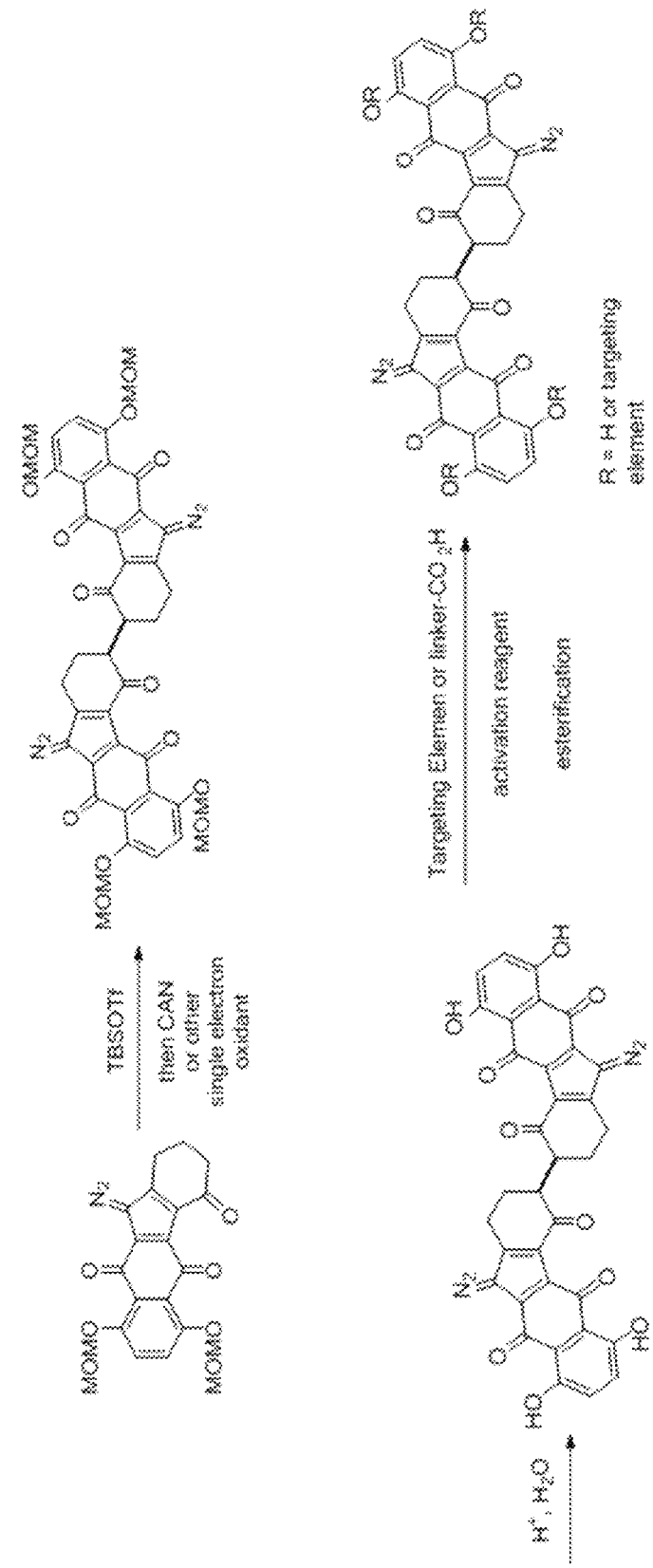

Other ILM groups may also be readily prepared. For example, pursuant to the synthetic chemical scheme set forth in FIG. 5, the four-membered deoxy polycyclic compound of FIG. 5 is modified to provide a diazo moiety in the five membered ring using chemical synthetic steps previously described and the resulting diazo compound is condensed with a protected carbohydrate compound using previously described synthetic steps to provide the deoxy four-membered ring intermediate of FIG. 5. Using analogous steps, this intermediate may be dimerized, bonded to a carbohydrate and/or linked to one or more linker CCTM groups to provide dimeric compounds according to the present invention containing one or more linker-CCTM groups. FIG. 7 shows an exemplary series of steps wherein a diazo substituted four membered fused cyclic compound is dimerized using previously described synthetic steps, deprotected using standing methodology and then linked to linker-CCTM groups at one or more hydroxyl groups which are available for coupling with a functional group on the linker-CCTM group.

Figure 8:
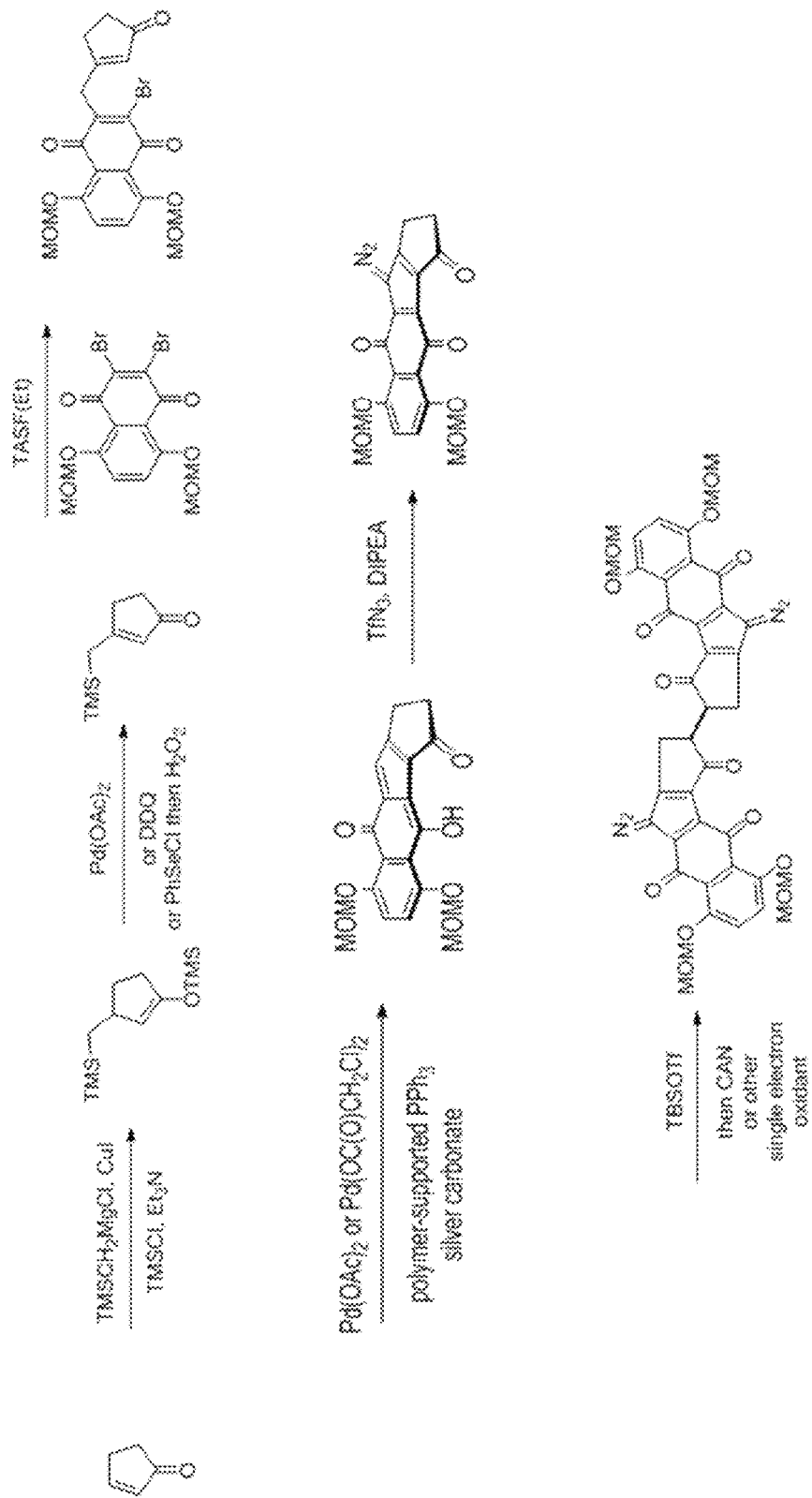
Figure 9:
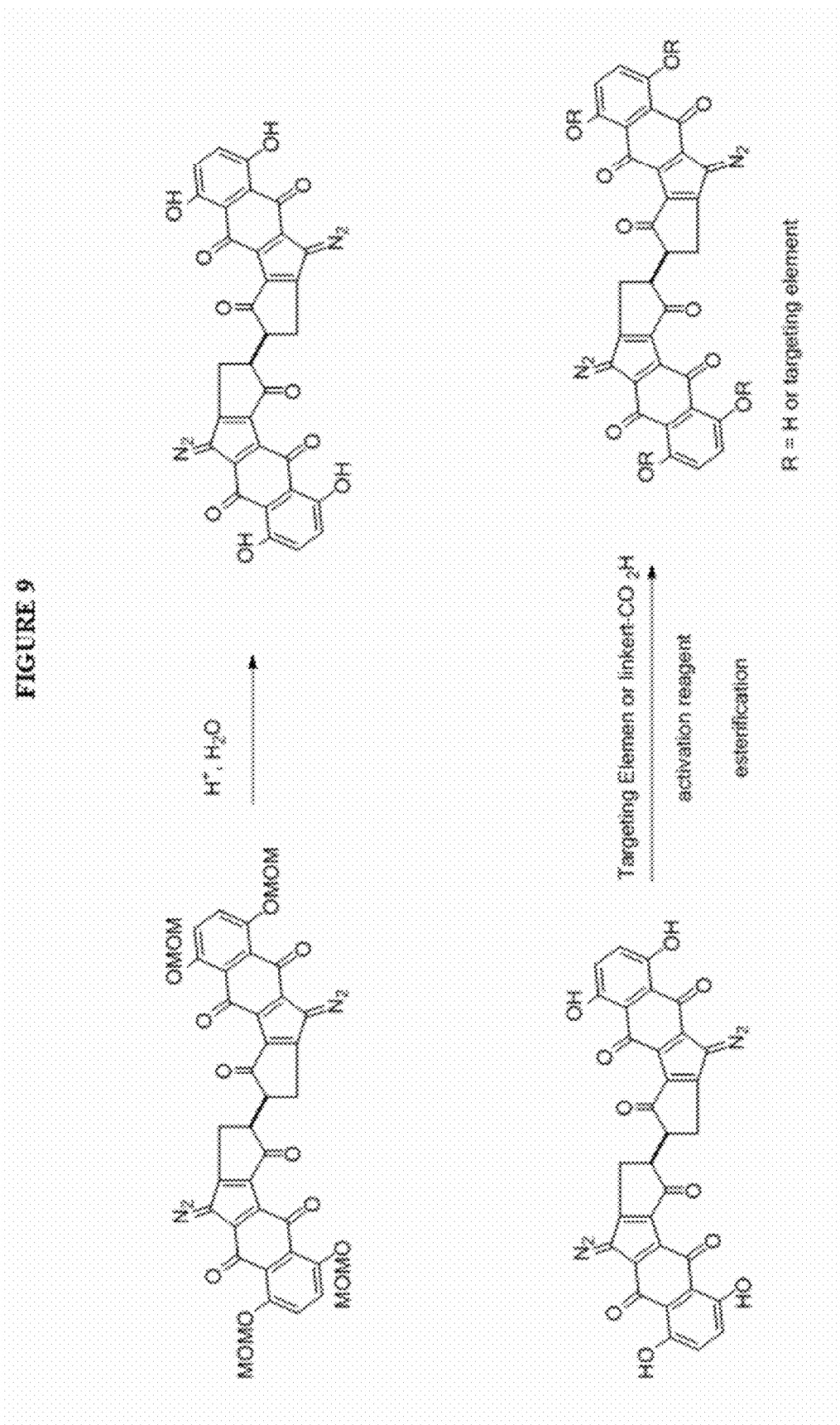

FIGS. 8 and 9 exemplify the steps for introducing a cyclopentanone group on the ILM group starting from the cyclopentanone and producing the four membered ring compound which is diazo substituted and eventually dimerized using methods which have been previously described. The dimerized compound is then coupled to at least one linker-CCTM groups at the available free hydroxyl group(s).

Figure 10:
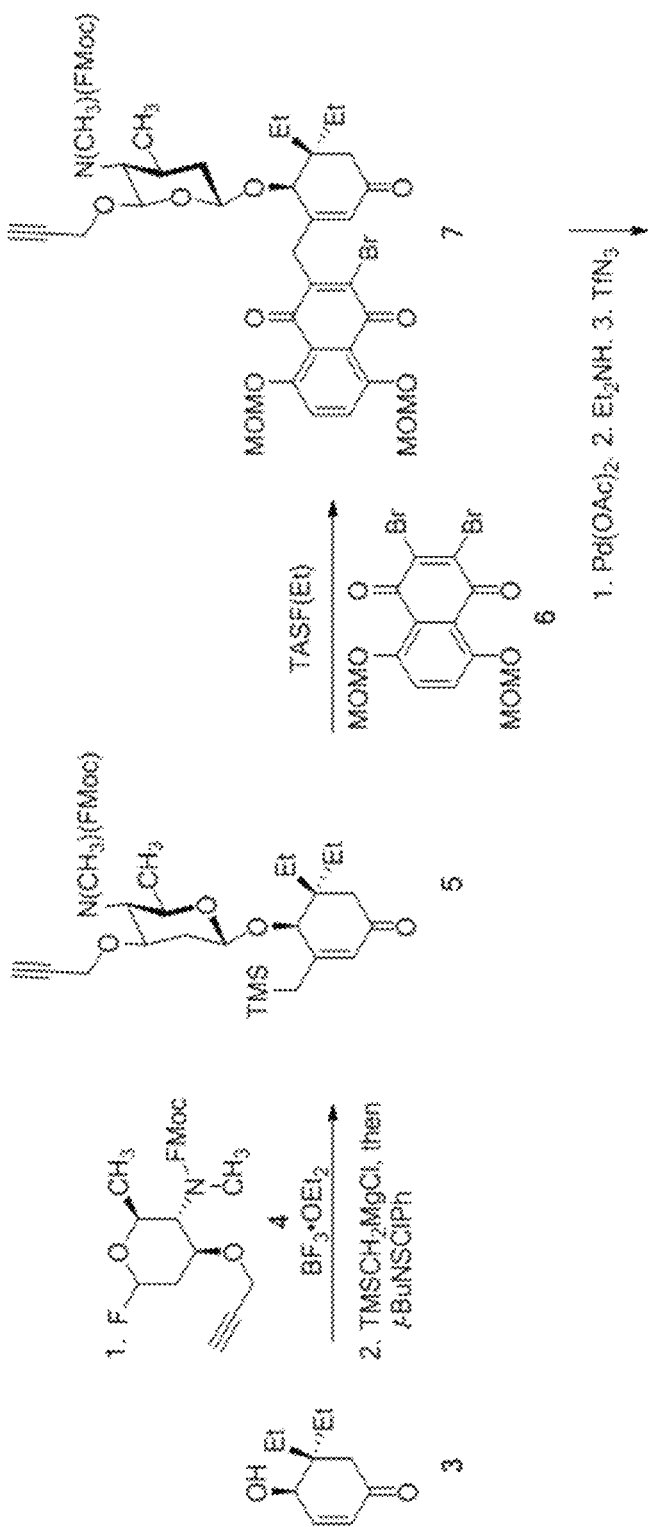
Figure 11:
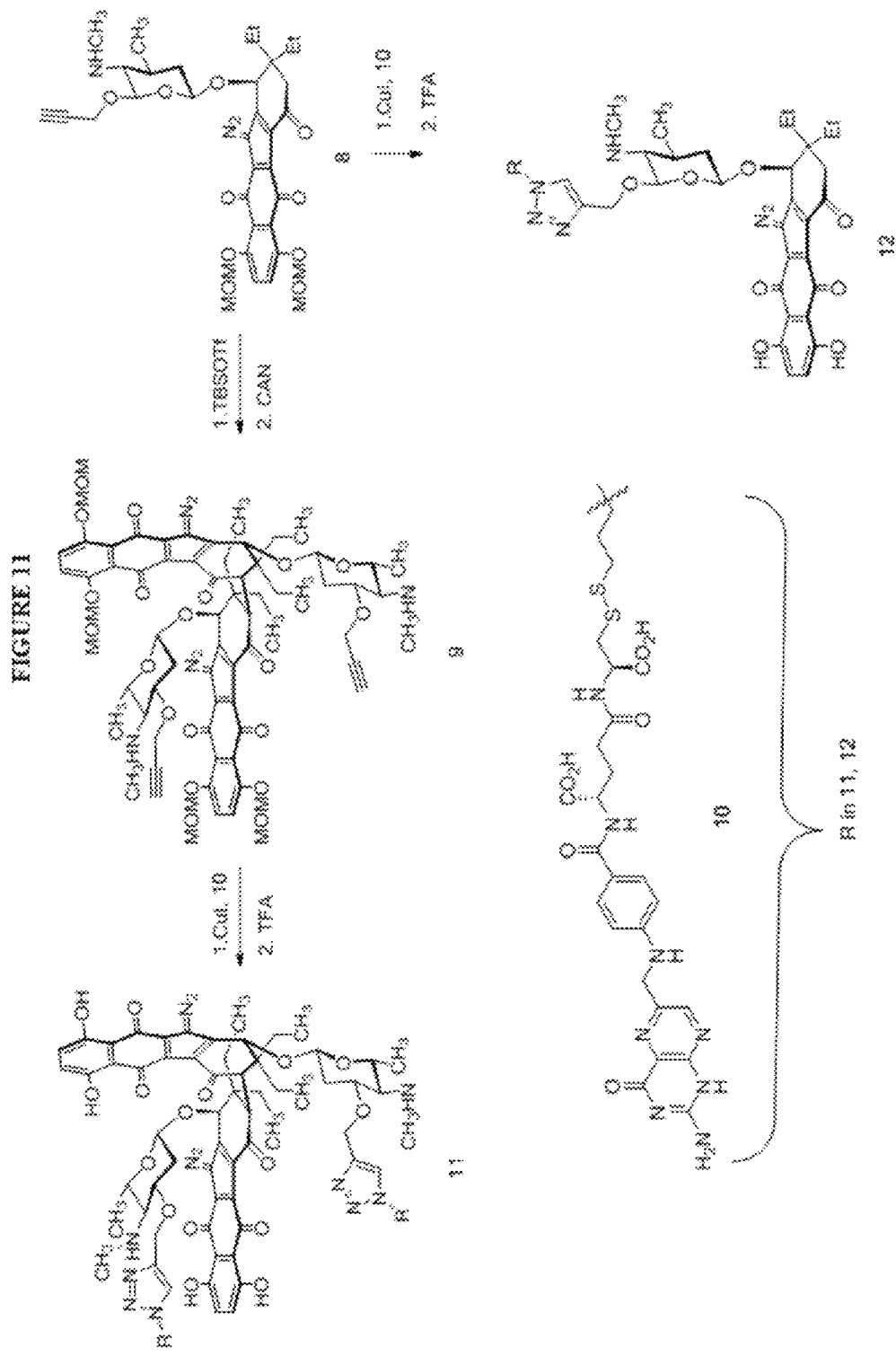

FIG. 10 shows a chemical synthetic approach which builds a linker through a triazole connector group [CON] by reacting the dialkylated cyclohexenone alcohol 3 with a carbohydrate analog 4 which has been derivatized to contain a propene group and a TMS-protected alkyl vinyl group 5 which is used to covalently link dibromo compound 6 using TASF(Et) in a reaction described above (see above and FIG. 3). The resulting compound 7 contains a propene group on the carbohydrate moiety which can be used to form a triazole [CON] group as part of a linker group or directly to a CCTM group. Compound 7 is cyclized to compound 8 of FIG. 11 using the previously described method which is dimerized to provide compound 9 and coupled to cleavable linker folate compound 10 through the reaction of an azido group of compound 10 (not shown) with the propene group to form the triazole moiety in compound 11. Alternatively, compound 8 may be reacted with compound 10 containing an azido group (not shown) to provide compound 12, a dimeric compound containing an ILM group and a CCTM group.

Figure 12:
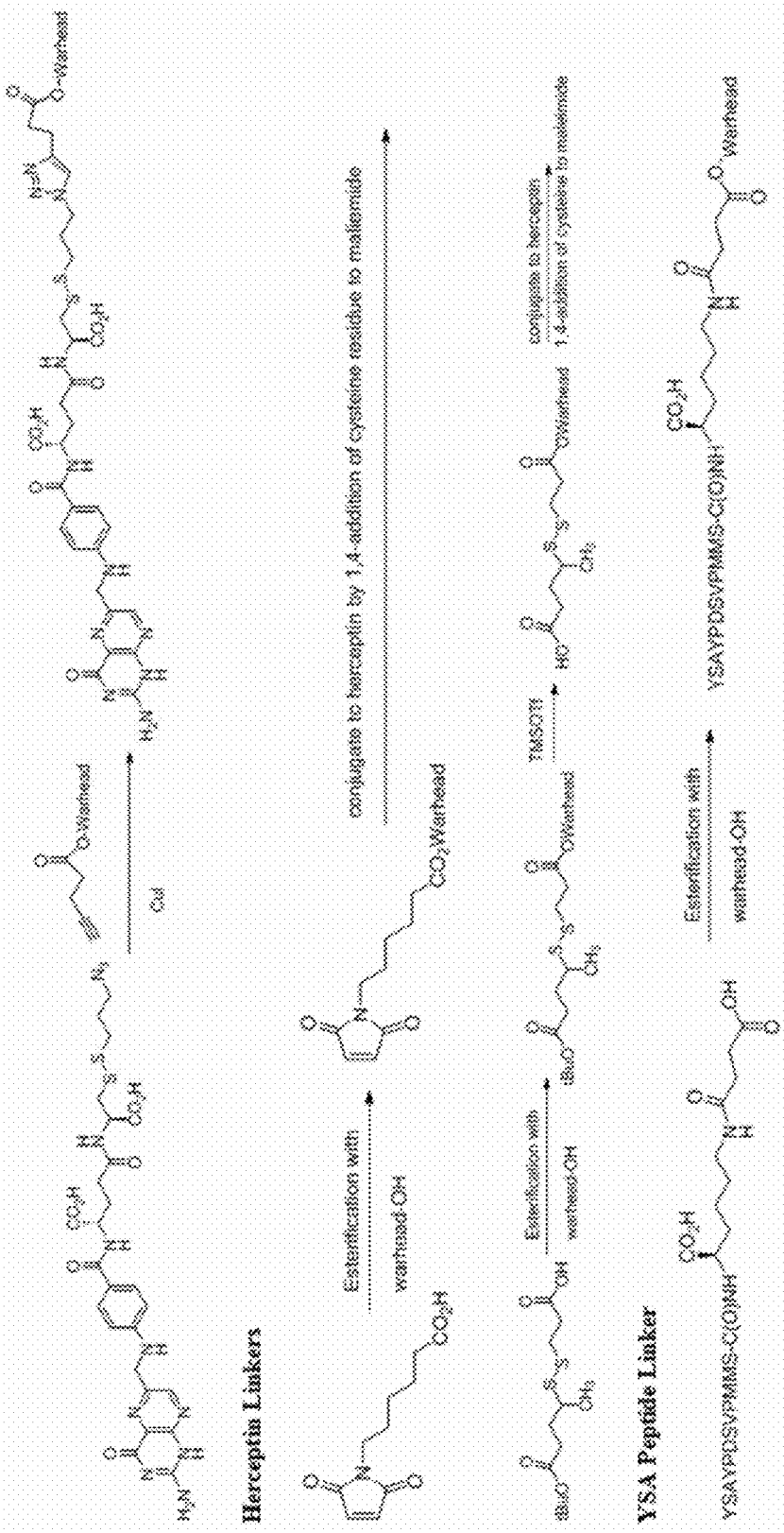
Figure 13:
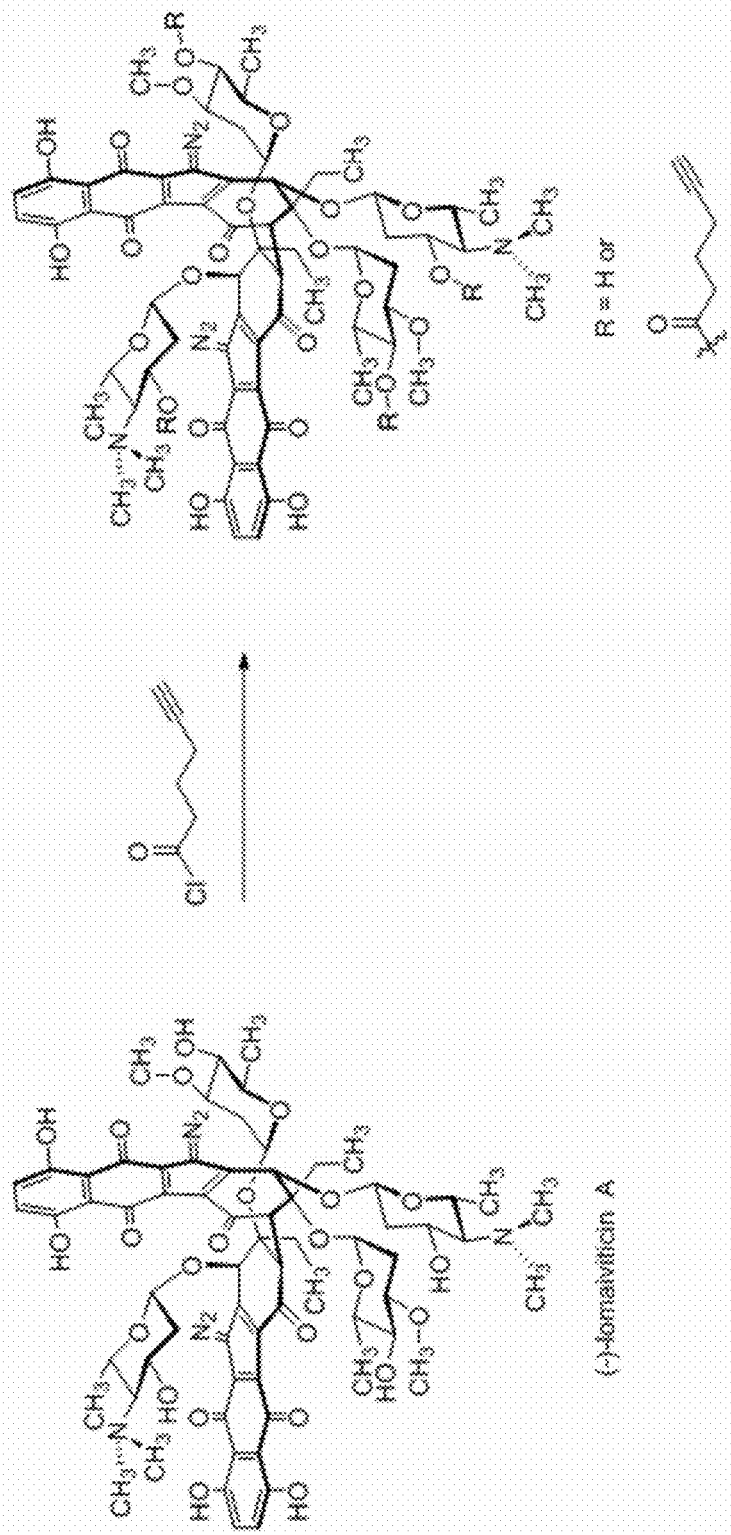
Figure 14:
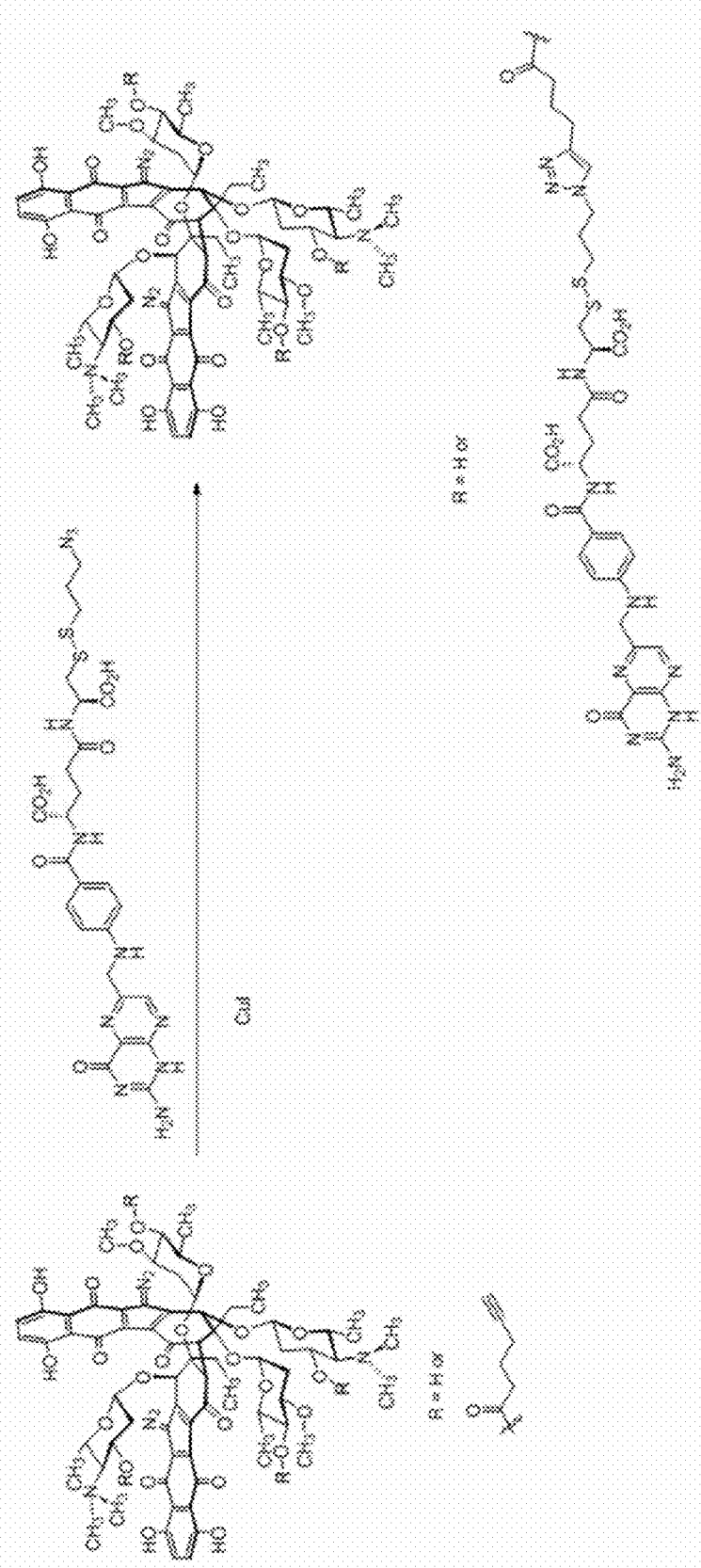
Figure 16:
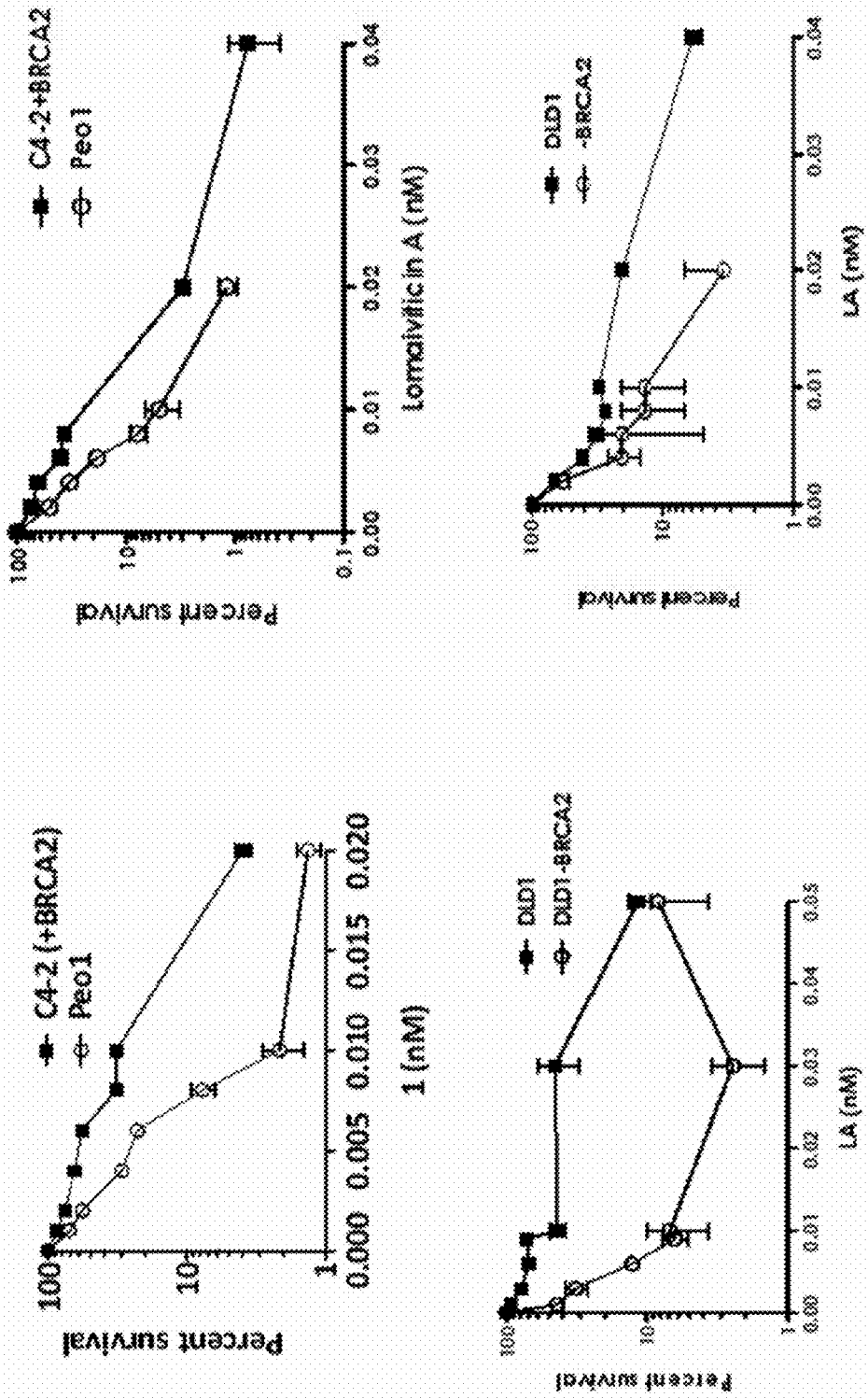
FIGS. 16-24 shows the effects of (−)-lomaiviticin A (LA) on various cancer cell lines which exhibit reduced expression of a number of DNA repair factors as indicated in each figure.
Figure 17:
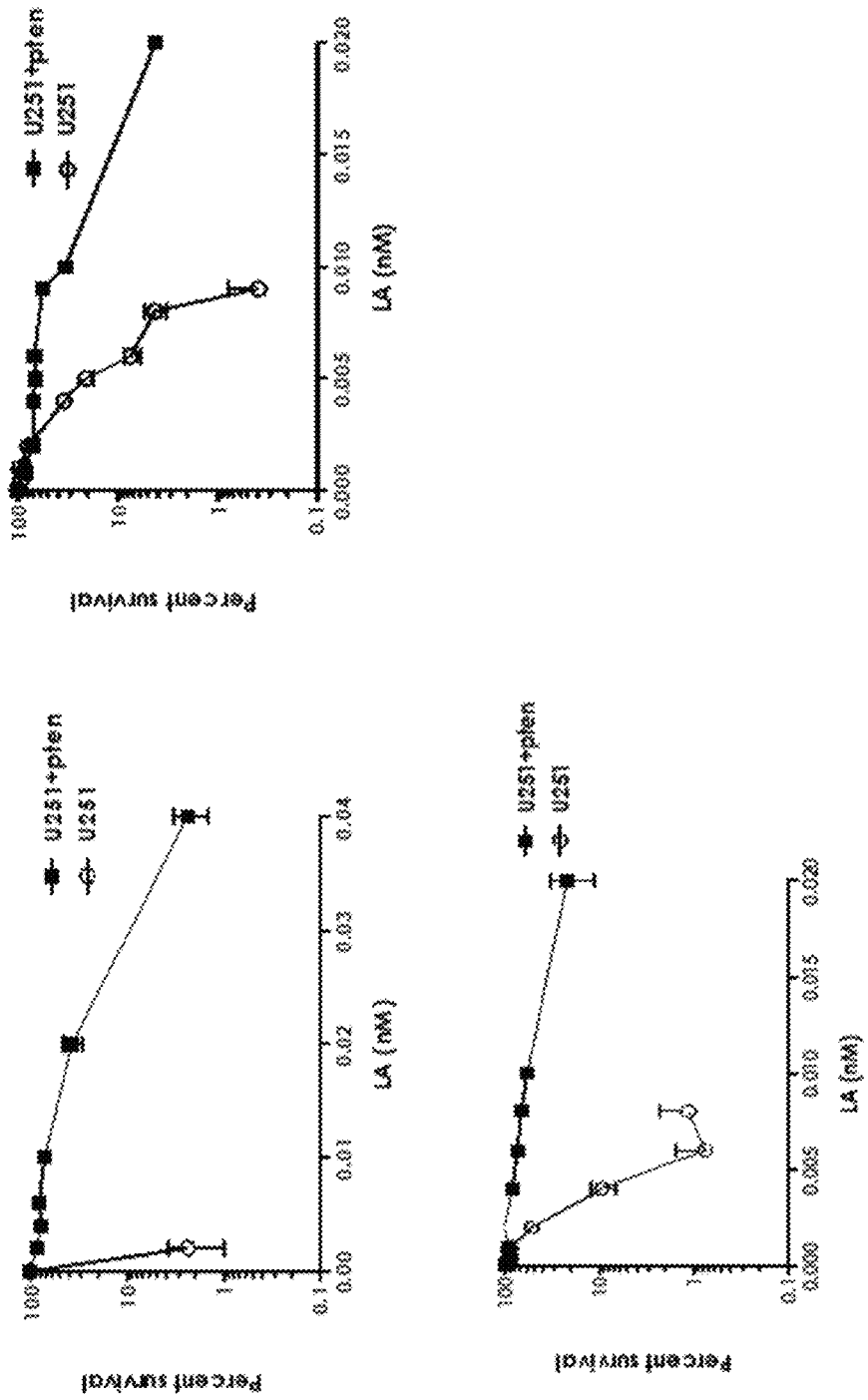
Figure 18:
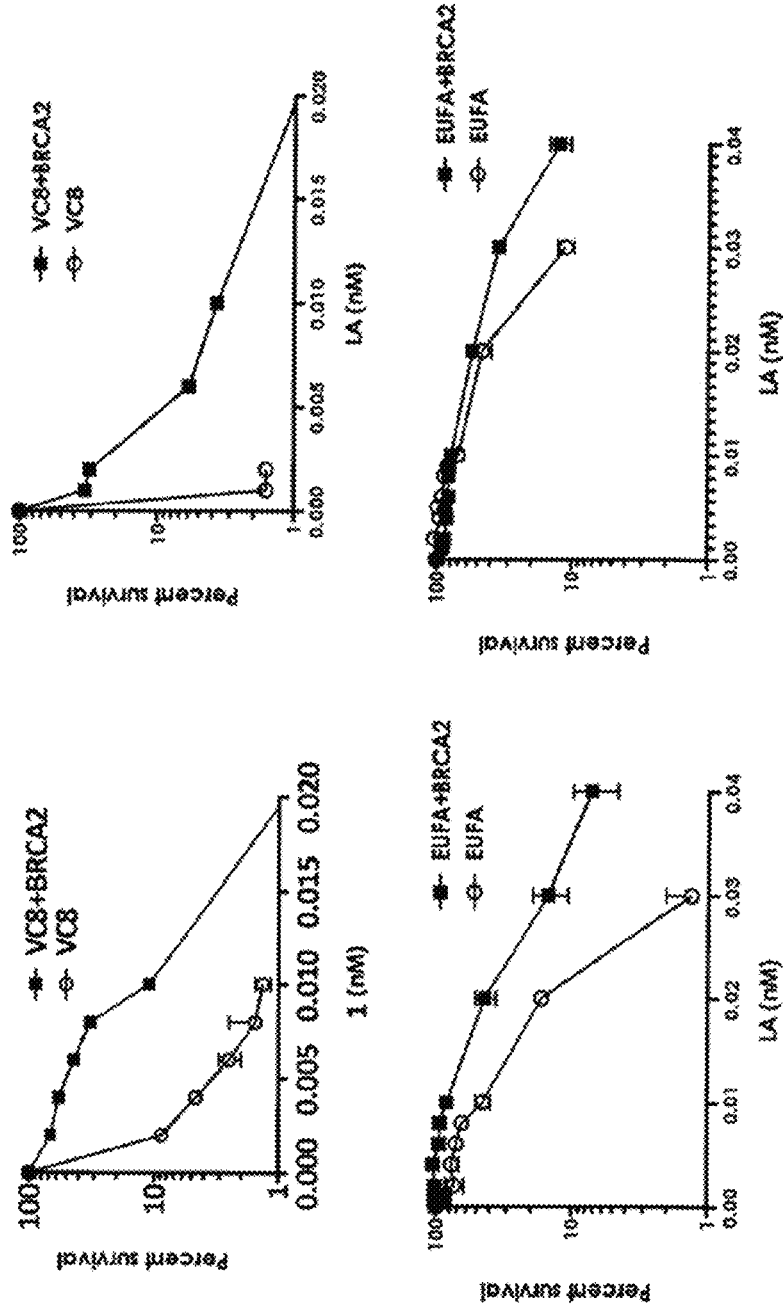
Figure 19:
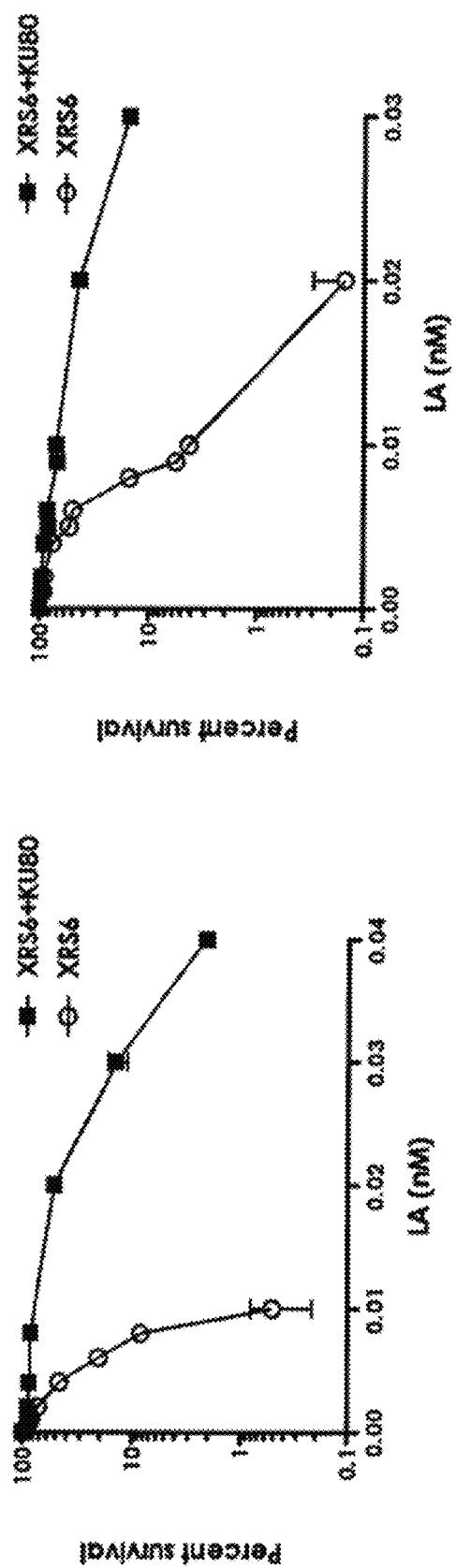
Figure 20:
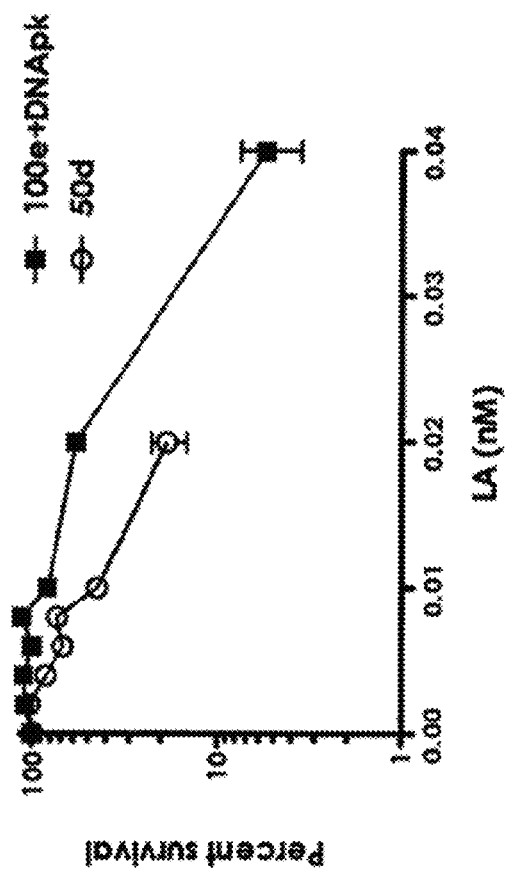
Figure 21:
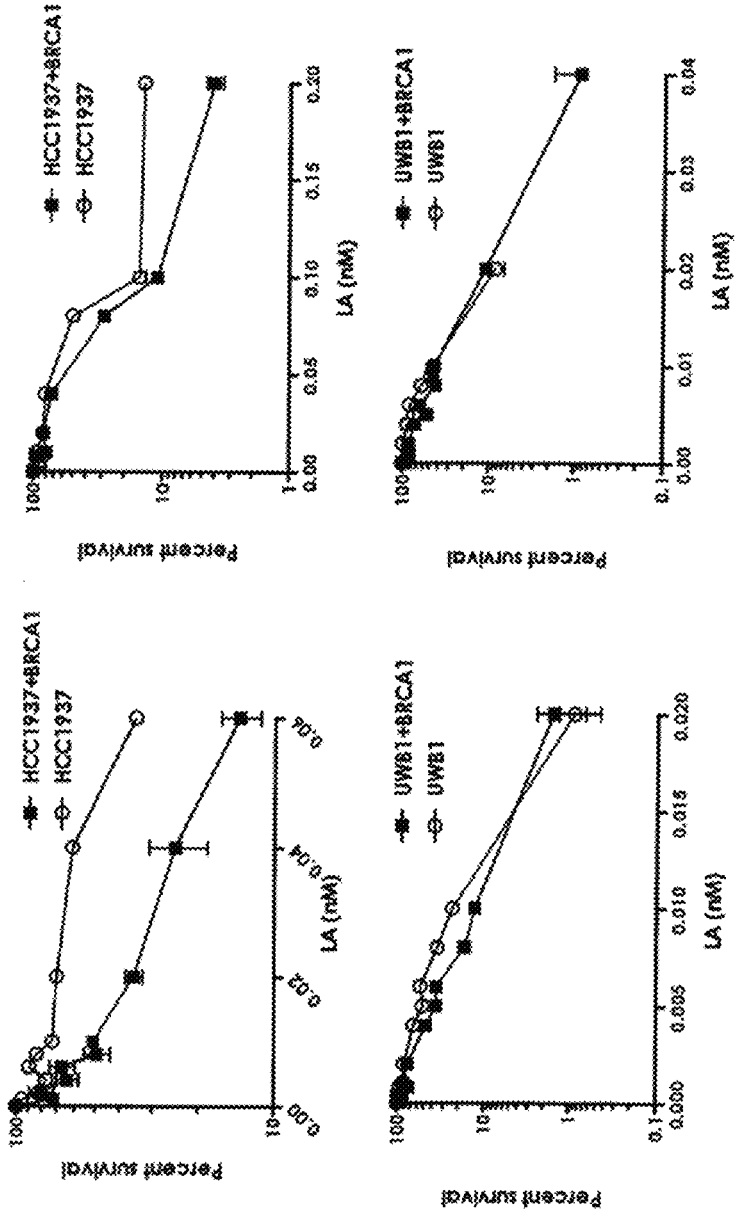
Figure 22:
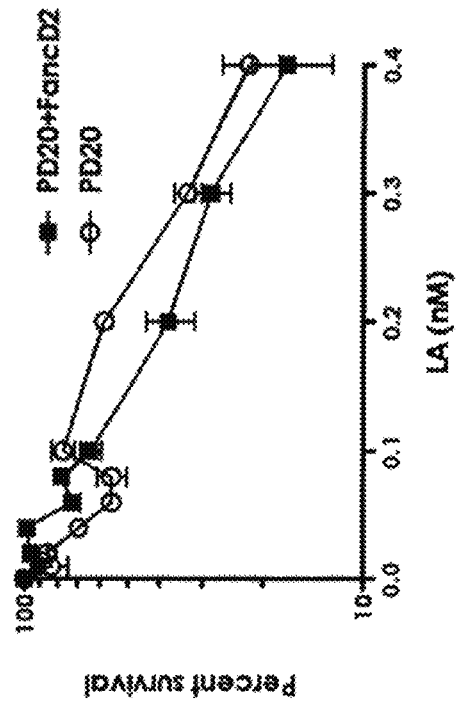
Figure 23:
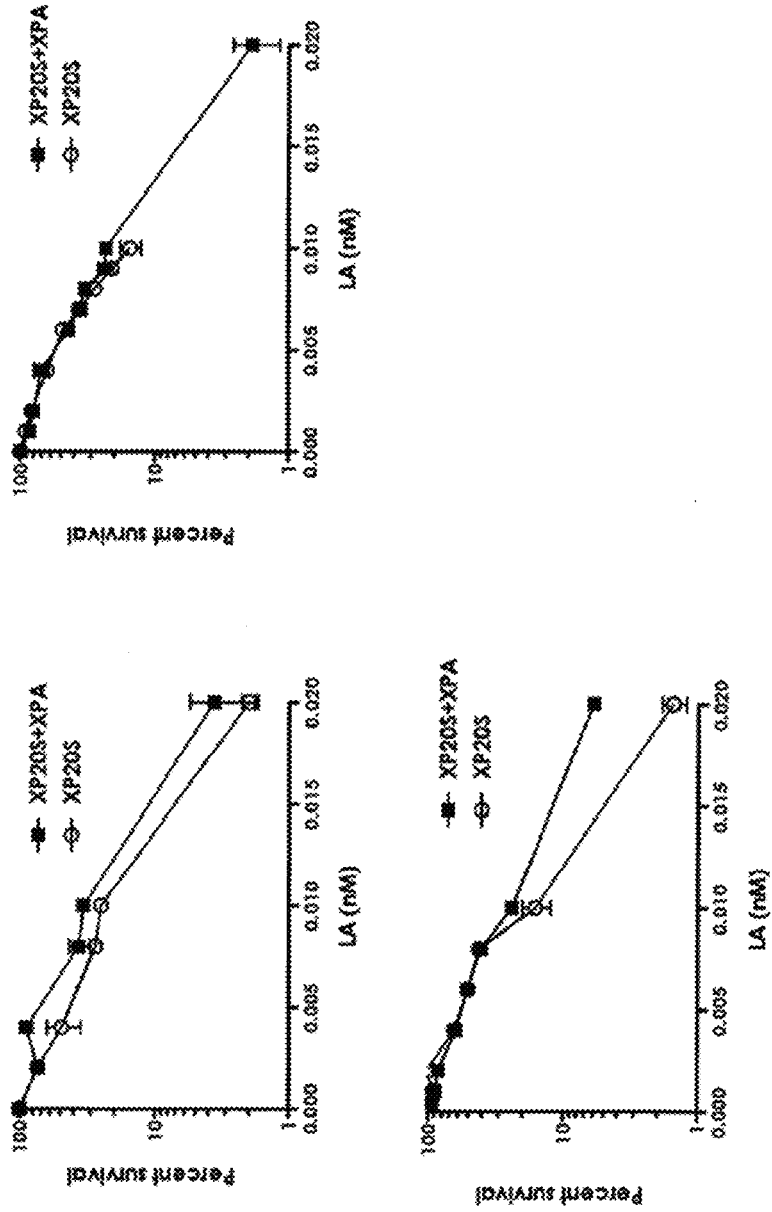
Figure 24:
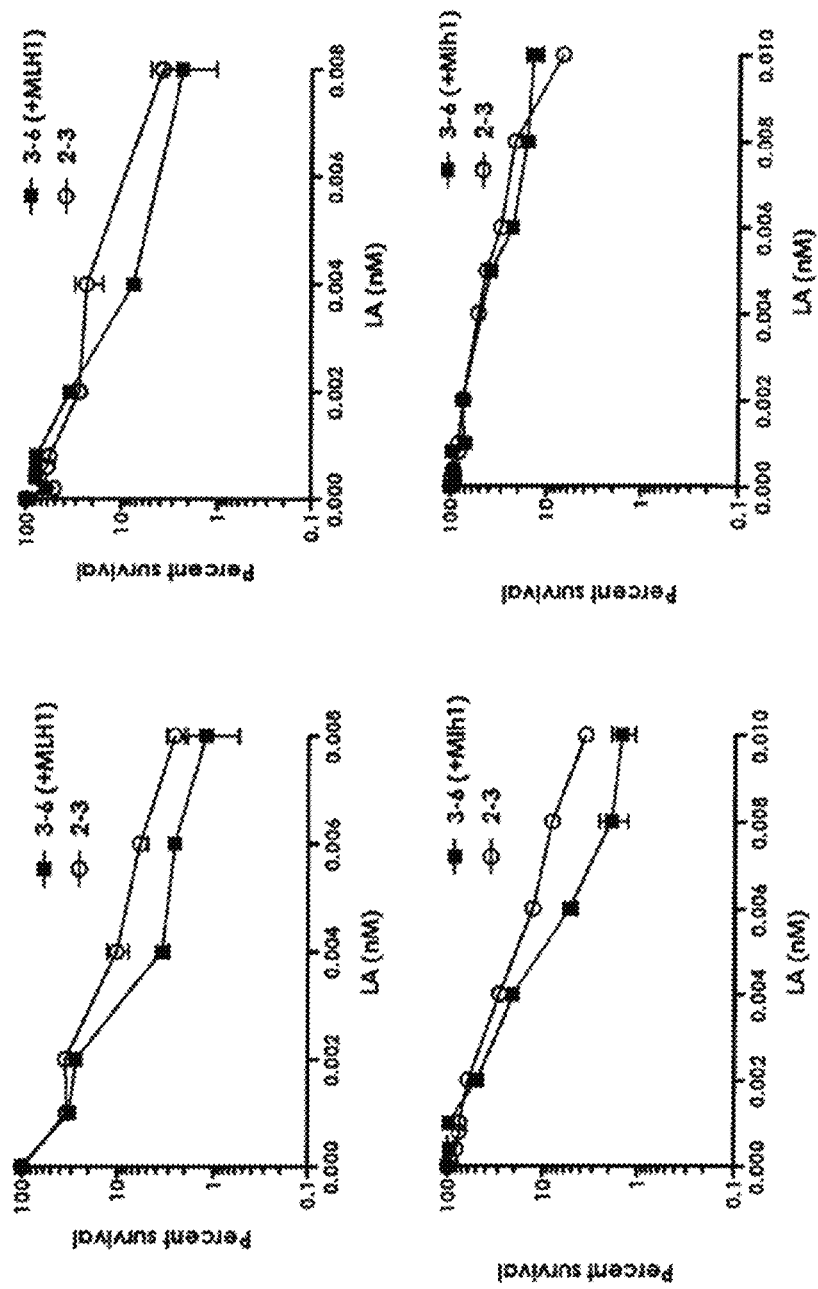

FIG. 12 shows several facile reactions to link a folate, herceptin or YSA peptide CCTM group through cleavable or noncleavable linkers with an ILM group (depicted as Warhead) as otherwise disclosed herein. FIGS. 13 and 14 show Lomaivitacin A derivatives (ILM group) which are linked to a CCTM group through the formation of an ester containing an alkyne group on the free hydroxyls of Lomaiviticin A, which alkyne group may be readily coupled onto the azido group of the linker-folate intermediate (FIG. 14) to provide the complex compound comprising a Lomaiviticin A (ILM)

group and a number of cleavable linker groups covalently attached to a folate CTM group.

Various compounds according to the present invention may be readily synthesized using techniques which are described hereinabove and as applied using standard synthetic chemical techniques.

By way of the following examples, further detailed description of the present invention is made. These should not be taken to limit the present invention in any way.

Biological Assays

Chronogenic Survival Assays

A number of cancer cells lines were tested for effectness of (−)-lomaiviticin A or MK7-206. These cell lines are DNA damage response deficient cells (DDR-deficient cancer cells, indicated in FIGS. 16-24) or hypoxic cells (indicated in FIG. 25). The indicated cells were seeded at 500 cells per well in 6-23ll dishes and treated with various concentrations of (−)-lomaiviticin A at the indicated concentrations indicated in FIGS. 16-25 for a period of 24 hours, after which time the media containing the inhibitor was removed and replaced with fresh media. Colonies were fixed with 0.9% saline solution and stained with crystal violet 8-14 days later. Colonies consistent of greater than 50 cells were counted. Experiments utilizing MK7-206 for the cell lines which are presented in attached FIG. 28 (Table 2) and FIG. 30 (Table 4) were also conducted (at higher concentrations than for (−)lomaiviticin A). MK7-206 showed similar efficacy to LA, but at a higher concentration.

Western Blotting

MCF-7 are seeded into 6-well dishes and treated with various doses of (−)-lomaiviticin A (LA), in the absence and presence of ionizing radiation (IR) at a dose rate of 2.4295 Gy/min (2 Gy, X-Ray) for 24 hour. After treatment, the cells were harvested for lysis in AZ lysis buffer (50 nM Tris, 250 mM NaCl, 1% Igepal, 0.1% SDS, 5 mM EDTA, 10 mM $Na_4P_2O_7$, 10 mM NaF) containing protease and phosphatase inhibitors. Western blotting was performed (FIG. 26).

Primary antibodies used were: mouse monoclonal anti-Ser1981-pATM (10H11.E12, Millipore, Temecula, Calif.), mouse monoclonal anti-vinculin (SPM227, Abcam, Cambridge, Mass.), rabbit polyclonal anti-Ser428-pATR (Cell Signaling, Danvers, Mass.), rabbit polyclonal anti-Thr68-pCHK2 (Cell Signaling), rabbit monoclonal anti-CHK2 (D9C6, Cell Signaling), rabbit monoclonal anti-Ser345-pCHK1 (Cell Signaling), and rabbit monoclonal anti-CHK1 (E250, Millipore).

Proteins were visualized with horseradish peroxidase-conjugated anti-mouse and anti-rabbit immunoglobulin G (Thermo Scientific, Rockford, Ill.) and the SuperSignal West Pico Chemiluminescent Substrate detection system (Thermo Scientific).

Results:

The results of the above-described experiments are presented in attached FIGS. 16-27. The various experiments evidenced that cells which were DDR-deficient (BRCA2, pten, KU80 and DNApk) were more sensitive to (−)-lomaiviticin A. In addition, hypoxic cells, as evidenced by the effect of (−)-lomaiviticin A (LA) on hypoxic MCF7 and A549 cells (FIG. 25) are more sensitive to (−)-lomaiviticin A (LA) than are the normoxic cells. (−)-lomaiviticin A (LA) treated MCF7 cells showed an increase in pATM and pCHK2, but not pATR and pCHK1 (FIG. 26).

The results of the experiments conducted and presented in FIGS. 16-24 shows that numerous DDR-deficient cancer cells are particularly susceptible to (−)-lomaiviticin A (LA), representing a treatment option for cancer patients. FIGS. 27-30, Tables 1-3 summarizes the results of the experiments which are presented in FIGS. 16-25.

FIGS. 27-30 evidence that both (−) lomaiviticin A and MK7-206 show excellent efficacy against cell lines in which certain DNA damage repair systems are deficient or down regulated. These two agents also exhibit or are expected to exhibit potent efficacy against hypoxic cells.

The invention claimed is:

1. A compound according to the chemical structure:

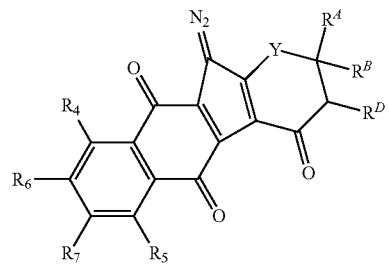

where Y is a bond or CH—$R^S$ group;

$R_4$ is OH, $C_1$-$C_3$ alkyl group, a OC(O)—($C_1$-$C_3$) alkyl group, a C(O)O—($C_1$-$C_3$) alkyl group or L-CCTM;

$R_5$ is $C_1$-$C_3$ alkyl, O—($C_1$-$C_3$)alkyl, a OC(O)—($C_1$-$C_3$) alkyl group, a C(O)O—$C_1$-$C_3$) or L-CCTM;

$R_6$ and $R_7$ are each independently H, $C_1$-$C_3$ alkyl, OH, O—($C_1$-$C_3$)alkyl, halo (F, Cl, Br or I), a OC(O)—($C_1$-$C_3$) alkyl group, a C(O)O—$C_1$-$C_3$) or L-CCTM;

$R^A$ and $R^B$ are each independently H, $C_1$-$C_3$ alkyl (preferably, ethyl or H and ethyl) or L-CCTM;

$R^D$ is H, $C_1$-$C_3$ alkyl, O($C_1$-$C_3$) alkyl, an optionally substituted aryl group or forms a dimer compound with the compound to which $R^D$ is attached (in certain preferred embodiments, $R^D$ is H or the compound to which $R^D$ is attached and $R^D$ form a dimer)

$R^S$ is OH, a

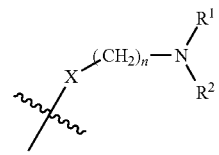

group where n is 0, 1, 2, 3, 4, or 5 and one or more of the methylene groups when present are optionally substituted with OH, $OCH_3$ or $CH_3$, or $R^S$ is a sugar moiety containing a 4-amino group which is optionally substituted with a L-CCTM group or one or two $C_1$-$C_3$ alkyl groups which alkyl groups may be optionally substituted with one or two alcohol groups, preferably $R^S$ is a sugar moiety according to the chemical structure:

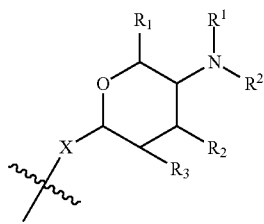

where X is O, S, N—$R^N$ or $CH_2$ (preferably O);

$R^N$ is H or a $C_1$-$C_3$ alkyl group (preferably H);

$R^1$ and $R^2$ are each independently H, a $C_1$-$C_3$ alkyl group optionally substituted with one or two alcohol groups (preferably methyl) or a L-CCTM group;

$R_1$, $R_2$ and $R_3$ are each independently H, OH, a halo group (F, Cl, Br, I), O—($C_1$-$C_3$)alkyl, a $C_1$-$C_3$ alkyl, a $C_2$-$C_4$ acyl group, a OC(O)—($C_1$-$C_3$) alkyl group, a C(O)O—$C_1$-$C_3$) alkyl group or a L-CCTM group;

L is a bond or a linker group; and

CCTM is a cancer cell targeting moiety which binds to a cancer cell, or a pharmaceutically acceptable salt or stereoisomer thereof.

2. The compound according to claim 1 wherein said CCTM group is a PSMA group according to the chemical structure:

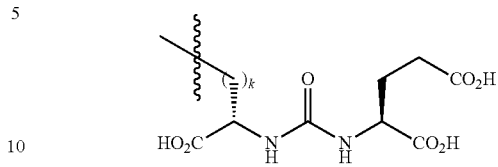

Where $X_1$ and $X_2$ are each independently $CH_2$, O, NH or S;

$X_3$ is O, $CH_2$, $NR^1$, S(O), S(O)$_2$, —S(O)$_2$O, —OS(O)$_2$, or OS(O)$_2$O;

$R^1$ is H, a $C_1$-$C_3$ alkyl group, or a —C(O)($C_1$-$C_3$) group; and k is an integer from 0 to 20;

or a salt or stereoisomer thereof.

3. The compound according to claim 2 wherein said PSMA binding group is the group

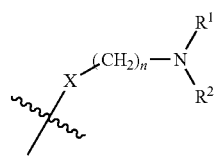

or a salt or stereoisomer thereof.

4. The compound according to claim 1 where $R^S$ is a

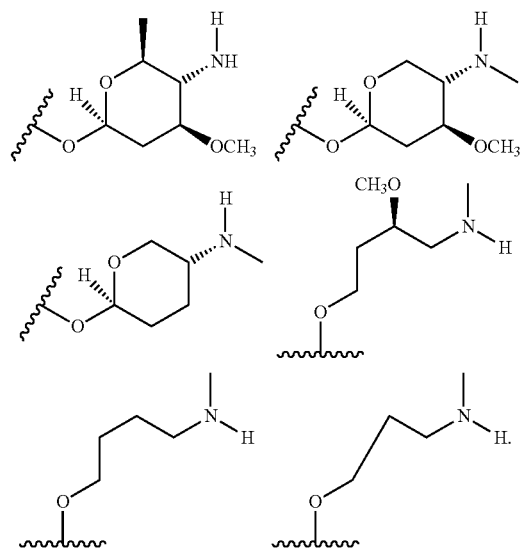

group where n is 0, 1, 2, 3, 4, or 5 and one or more of the methylene groups when present are optionally substituted with OH or $CH_3$, or $R^S$ is a sugar moiety containing a 4-amino group which is optionally substituted with a L-CCTM group or one or two $C_1$-$C_3$ alkyl groups which alkyl groups may be optionally substituted with one or two alcohol groups.

5. The compound according to claim 1 wherein $R^S$ is a group according to the chemical structure:

6. A pharmaceutical composition comprising an effective amount of a compound according to claim 1 in combination with a pharmaceutically acceptable carrier, additive and excipient and optionally in further combination with another anticancer agent.

7. The composition according to claim 6 wherein said additional anticancer agent is an antimetabolite, an inhibitor of topoisomerase I and II, an alkylating agent, a microtubule inhibitor or a mixture thereof.

8. The compound according to claim 1 wherein the chemical structure:
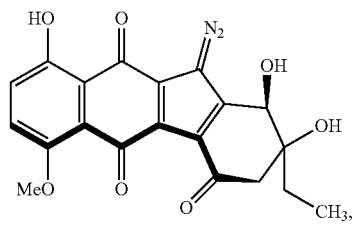
Or a stereoisomer thereof.